US011845993B2

(12) United States Patent
Salami et al.

(10) Patent No.: US 11,845,993 B2
(45) Date of Patent: Dec. 19, 2023

(54) METHODS FOR IDENTIFYING PROSTATE CANCER

(71) Applicant: THE REGENTS OF THE UNIVERSITY OF MICHIGAN, Ann Arbor, MI (US)

(72) Inventors: Simpa Salami, Ann Arbor, MI (US); Ganesh Palapattu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 11 days.

(21) Appl. No.: 17/209,892

(22) Filed: Mar. 23, 2021

(65) Prior Publication Data

US 2021/0324476 A1    Oct. 21, 2021

Related U.S. Application Data

(60) Provisional application No. 62/993,742, filed on Mar. 24, 2020.

(51) Int. Cl.
*C12Q 1/6886* (2018.01)
(52) U.S. Cl.
CPC ..... *C12Q 1/6886* (2013.01); *C12Q 2600/158* (2013.01); *C12Q 2600/16* (2013.01)
(58) Field of Classification Search
None
See application file for complete search history.

(56) References Cited

U.S. PATENT DOCUMENTS

2016/0097105 A1* 4/2016 Shak ............... C12Q 1/6886
435/6.12
2018/0148794 A1* 5/2018 Hoffmann ......... C12Q 1/6886

OTHER PUBLICATIONS

Cancer Research UK, "Multiparametric MRI (mpMRI) scan for prostate cancer," 2022, available via URL: < cancerresearchuk.org/about-cancer/cancer-in-general/tests/multiparametric-mri>, (Year: 2022).*
Salami et al Eur Urol. Suppl Mar. 2017. 16(3): e1063, abstract 616 (Year: 2017).*
Salami et al. JCO Precis Oncol. Jun. 12, 2019, p. 1-12, available via URL: <ascopubs.org/doi/pdf/10.1200/PO.19.00054?role=tab> (Year: 2019).*
Salami et al. J Urology. 2019. vol. 201. No. 4S Supplement, e179-e180, abstract MP13-08 (Year: 2019).*
Salami et al J Urology. May 2017. vol. 197, No. 4S Supplement, e595, abstract PD33-05 (Year: 2017).*
Houlahan et al European Urology. Jul. 2019. 76: 18-23 and Supplemental Information, 25 pages total (Year: 2019).*
Rubicz et al (Molecular Oncology. Oct. 2016. 11: 140-150 (Year: 2016).*
Abate-Shen et al., Molecular genetics of prostate cancer. Genes Dev. Oct. 1, 2000;14(19):2410-34.
Johnson et al., Detection of Individual Prostate Cancer Foci via Multiparametric Magnetic Resonance Imaging. Eur Urol. May 2019;75(5):712-720.
Le et al., Multifocality and prostate cancer detection by multiparametric magnetic resonance imaging: correlation with whole-mount histopathology. Eur Urol. Mar. 2015;67(3):569-76.
Lee et al., Molecular alterations in prostate cancer and association with MRI features. Prostate Cancer Prostatic Dis. Dec. 2017;20(4):430-435.
Mccann et al., Quantitative Multiparametric MRI Features and PTEN Expression of Peripheral Zone Prostate Cancer: A Pilot Study. AJR Am J Roentgenol. Mar. 2016;206(3):559-65.
Palapattu et al., Molecular Profiling to Determine Clonality of Serial Magnetic Resonance Imaging/Ultrasound Fusion Biopsies from Men on Active Surveillance for Low-Risk Prostate Cancer. Clin Cancer Res. Feb. 15, 2017;23(4):985-991.
Panebianco et al., Negative Multiparametric Magnetic Resonance Imaging for Prostate Cancer: What's Next? Eur Urol. Jul. 2018;74(1):48-54.
Parry et al., Genomic Evaluation of Multiparametric Magnetic Resonance Imaging-visible and -nonvisible Lesions in Clinically Localised Prostate Cancer. Eur Urol Oncol. Feb. 2019;2(1):1-11.
Ruijter et al., Molecular genetics and Molecular genetics and epidemiology of prostate carcinoma. Endocr Rev. Feb. 1999;20(1):22-45.
Salmasi et al., A 17-Gene Genomic Prostate Score Assay Provides Independent Information on Adverse Pathology in the Setting of Combined Multiparametric Magnetic Resonance Imaging Fusion Targeted and Systematic Prostate Biopsy. J Urol. Sep. 2018;200(3):564-572.
Truong et al., Impact of Gleason Subtype on Prostate Cancer Detection Using Multiparametric Magnetic Resonance Imaging: Correlation with Final Histopathology. J Urol. Aug. 2017;198(2):316-321.

* cited by examiner

*Primary Examiner* — Carla J Myers
(74) *Attorney, Agent, or Firm* — CASIMIR JONES, S.C.; Tanya A. Arenson

(57) ABSTRACT

Provided herein are compositions and methods for diagnosing and characterizing cancer. In particular, provided herein are compositions and methods for selecting MRI imaging methods for prostate tumors.

7 Claims, 15 Drawing Sheets
(14 of 15 Drawing Sheet(s) Filed in Color)

FIG. 4

METHODS FOR IDENTIFYING PROSTATE CANCER

CROSS-REFERENCE TO RELATED APPLICATIONS

This application claims the benefit of U.S. Provisional Patent Application No. 62/993,742, filed Mar. 24, 2020, the contents of which are incorporated by reference herein.

FIELD OF THE DISCLOSURE

Provided herein are compositions and methods for diagnosing and characterizing cancer. In particular, provided herein are compositions and methods for selecting MRI imaging methods for prostate tumors.

BACKGROUND OF THE DISCLOSURE

Afflicting one out of nine men over age 65, prostate cancer (PCa) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 181,500 American men will be diagnosed with PCa and 33,330 will die in 2020. The vast majority of patients diagnosed with PCa have an indolent course and do not die from the disease.

Distinguishing aggressive from indolent clinically localized PCa continues to pose a significant clinical challenge. Recent efforts to overcome this have involved the development and optimization of several diagnostic strategies, including multiparametric magnetic resonance imaging (mpMRI). mpMRI permits visual identification of areas that are suggestive for intermediate to high-grade cancer. The emergence of various MRI/ultrasound fusion biopsy platforms has led to increased detection of aggressive PCa by facilitating targeted biopsy of visible lesions.1-6 As a result, mpMRI is now widely used in guiding treatment decisions in men with clinically localized disease, especially when selecting patients suitable for active surveillance or potentially focal therapy.7-10 The prevailing view is that only mpMRI-visible cancers require clinical action. However, use of mpMRI in the evaluation of men with PCa is limited by cancer multifocality and interfocal disease heterogeneity. Individual patients are known to harbor multiple spatially distinct PCa foci with varying clinical, radiographic, and pathologic characteristics.11-15 Up to 55% of all PCa foci and 35% of clinically significant foci are not visible on mpMRI.3,16,17 Furthermore, more than 35% of lesions 1 cm or larger are missed by mpMRI.17 Although some studies have demonstrated that up to 50% of mpMRI invisible PCa may harbor relevant genomic alterations, the clinical and prognostic significance of mpMRI invisible PCa remains unknown.18 An improved understanding of the molecular characteristics and clinical trajectories of mpMRI-visible and -invisible cancers facilitates more optimal treatment allocation. For example, if mpMRI-invisible foci are found to be biologically indolent, those with a known diagnosis of low-grade disease and a negative mpMRI could be directed toward active surveillance. Similarly, those with a single lesion detected on mpMRI could be more confidently directed toward focal therapy, with low concern for missing a clinically relevant lesion.

What is needed are techniques for determining the MRI visibility of prostate lesions.

SUMMARY OF THE DISCLOSURE

Provided herein are compositions and methods for diagnosing and characterizing cancer. In particular, provided herein are compositions and methods for selecting MRI imaging methods for prostate tumors.

The compositions and methods described herein provide guidance as to whether or not prostate tumor can be analyzed using MRI imaging. Such methods reduce or eliminate false negatives caused by non-visible tumors and reduce costly imaging methods for non-visible tumors.

For example, in some embodiments, provided herein is a method of performing an MRI imaging on a subject suspected of having prostate cancer (e.g., aggressive prostate cancer), comprising: a) detecting the presence of altered expression of one or more genes (e.g., 1, 2, 3, 4, 5, 6, 7, 8, 9, or 10 genes) selected from AMACR, TPM2, GSN, DST, SRD5A2, SGK1, S100A6, MYLK, or KLK2 in a sample from said subject; and b) performing MRI imaging on the subject when altered expression of the genes is detected.

In further embodiments, provided herein is a method of recommending an imaging method to a subject suspected of having prostate cancer, comprising: a) receiving a sample from a subject; b) detecting the presence of altered expression of one or more genes selected from, for example, AMACR, TPM2, GSN, DST, SRD5A2, SGK1, S100A6, MYLK, or KLK2 in a sample from said subject; and c) recommending MRI imaging on the subject when altered expression is detected.

Additional embodiments provide a method of performing a prostate cancer detection assay on a subject suspected of having prostate cancer, comprising: a) detecting or having detected the presence or absence of altered expression of one or more genes selected from, for example, AMACR, TPM2, GSN, DST, SRD5A2, SGK1, S100A6, MYLK, or KLK2 in a sample from the subject; and b) performing nom-MRI imaging or prostate biopsy on the subject when the absence of altered expression is detected.

In some embodiments, the altered expression is over or under expression relative to a control level (e.g., the level in a sample of a subject not suspected of having prostate cancer). In some embodiments, AMACR and KLK2 are overexpressed in MRI visible tumor and DST, GSN, MYLK, S100A6, SGK1, SRD5A2, TPM2 are underexpressed in MRI visible tumors. In some embodiments, the genes are over or underexpressed by a log 2-fold change of 1 to 2.5. In some embodiments, the genes are SRD5A2, GSN, DST, and SGK1. In some embodiments, the method comprises not performing said MRI imaging when altered expression is not detected (e.g., performing a non-MRI imaging method is performed instead). The present disclosure is not limited to particular MRI methods. In some exemplary methods, the MRI is multi-parametric MRI (mpMRI).

The present disclosure is not limited to particular sample types. Examples include, but are not limited to, tissue (e.g., prostate tissue), urine, or blood.

Further embodiments provide a kit, comprising: reagents for detecting the level of expression of two or more genes (e.g., 2, 3, 4, 5, 6, 7, 8, 9, 10, 2-10, 3-10, 4-10, 5-10, 6-10, 8-10, 9-10, 2-8, 3-8, 4-8, 5-8, 6-8, 7-8, 2-7, 3-7, 4-7, 5-7, 6-7, 2-6, 3-6, 4-6, 5-6, 2-5, 3-5, or 4-5 genes) selected from AMACR, TPM2, GSN, DST, SRD5A2, SGK1, S100A6, MYLK, or KLK2. The present disclosure is not limited to particular reagents. Examples include, but are not limited to, one or more nucleic acid primers and/or one or more nucleic acid probes. In some embodiments, the probes and/or primers comprise an exogenous label. In some embodiments, the primers and/or probes specifically bind to the genes.

Additional embodiments provide the use of a kit as described herein to identify MRI visible or MRI non-visible prostate tumors.

Other embodiments provide a kit as described herein for use in identifying MRI visible or MRI non-visible prostate tumors.

Additional embodiments will be apparent to persons skilled in the relevant art based on the teachings contained herein.

DESCRIPTION OF THE DRAWINGS

The patent or application file contains at least one drawing executed in color. Copies of this patent or patent application publication with color drawings will be provided by the Office upon request and payment of the necessary fee.

FIG. 4 shows multivariable analysis to assess the prognostic significance of predicted multiparametric magnetic resonance imaging (mpMRI) visibility status. Using data from the testing cohort described in FIG. 3 (Affymetrix microarray data matched to the distribution of the The Cancer Genome Atlas Prostate Adenocarcinoma RNAseq data; n=375), multivariable Cox proportional hazard models were developed to assess the capacity of predicted mpMRI visibility status to predict: (A) biochemical recurrence-free survival (BFS), (B) distant metastasis-free survival (DMFS), and (C) prostate cancer-specific mortality (PCSM), adjusting for relevant clinicopathological variables.

DEFINITIONS

Figure 1:
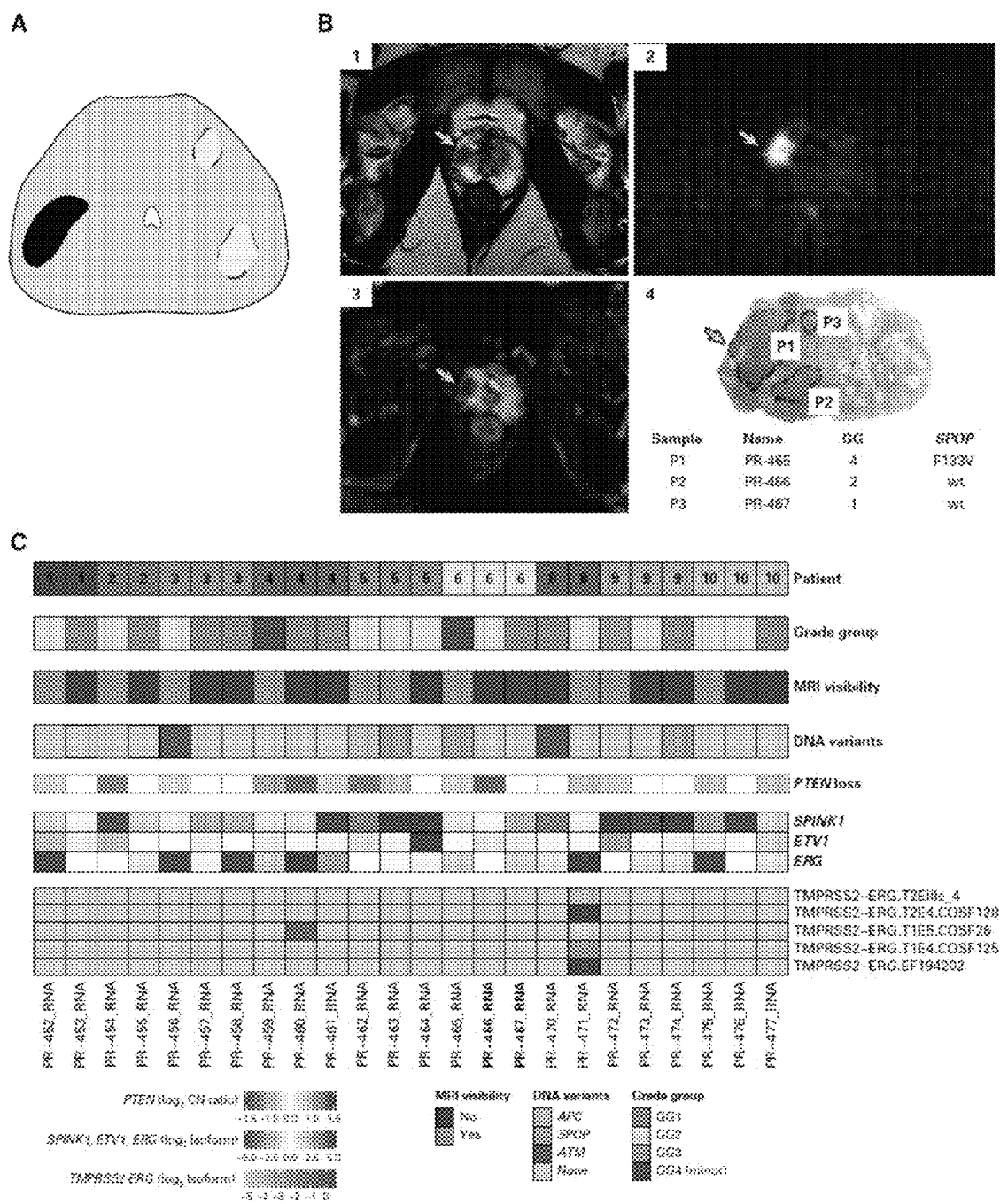
FIG. 1 shows radiogenomic characterization of multifocal prostate cancer. (A) Cartoon depicting multifocal prostate cancer (PCa) with both multiparametric magnetic resonance imaging (mpMRI)-visible (solid black, left) and invisible (gray with black discontinuous borders, right) lesions. (B) Coregistration of axial mpMRI images with whole-mount histopathology. (1) Axial high-resolution T2, (2) axial diffusion-weighted imaging (b-value=1,600), and (3) axial apparent diffusion coefficient map shows a visible lesion corresponding to cancer focus P1 (grade group [GG] 4; arrows) on the radical prostatectomy specimen (hematoxylin and eosin, panel 4). (C) Integrative summary of the primary multifocal PCa cohort.

To facilitate an understanding of the present disclosure, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized prostate cancer cells" is meant to refer to prostate cancer cells which have metastasized.

The term "neoplasm" as used herein refers to any new and abnormal growth of tissue. Thus, a neoplasm can be a benign or premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

DETAILED DESCRIPTION OF THE DISCLOSURE

Provided herein are compositions and methods for diagnosing and characterizing cancer. In particular, provided herein are compositions and methods for selecting MRI imaging methods for prostate tumors.

Accordingly, provided herein are compositions and methods for identifying prostate cancer lesions that are visible using MRI imaging methods. For example, in some embodiments, subjects found to have an expression profile indicative of MRI visible tumors are offered MRI imaging. However, subjects found to have an expression profile indicative of a non-visible tumor are offered a biopsy or other diagnostic option.

The present disclosure is not limited to particular MRI methods. In some exemplary methods, the MRI is multi-parametric MRI (mpMRI).

The present disclosure is not limited to particular genes. For example, in some embodiments, the genes are one or more genes (e.g., 3, 4, 5, 6, 7, 8, 9, 10, 2-10, 3-10, 4-10, 5-10, 6-10, 8-10, 9-10, 2-8, 3-8, 4-8, 5-8, 6-8, 7-8, 2-7, 3-7, 4-7, 5-7, 6-7, 2-6, 3-6, 4-6, 5-6, 2-5, 3-5, or 4-5 genes) selected from Alpha-Methylacyl-CoA Racemase (AMACR), Tropomyosin 2 (TPM2), Gelsolin (GSN), Dystonin (DST), Steroid 5 Alpha-Reductase 2 (SRD5A2), Serum/Glucocorticoid Regulated Kinase 1 (SGK1), S100 Calcium Binding Protein A6 (S100A6), Myosin Light Chain Kinase (MYLK), or Kallikrein Related Peptidase 2 (KLK2). In some embodiments, the genes are SRD5A2, GSN, DST, and SGK1. In some embodiments, over or under expression relative to a control level (e.g., the level in a sample of a subject not suspected of having prostate cancer) is indicative of an MRI visible tumor. In some embodiments, the presence of one or more polymorphisms and/or copy number variations in the genes is further detected.

In some embodiments, AMACR and KLK2 are overexpressed in MRI visible tumor and DST, GSN, MYLK, S100A6, SGK1, SRD5A2, TPM2 are underexpressed in MRI visible tumors.

Exemplary detection and analysis methods are described below.

Levels of mRNA can be quantitatively measured by northern blotting, which provides size and sequence information about the mRNA molecules. A sample of RNA is separated on an agarose gel and hybridized to a labeled RNA probe that is complementary to the target sequence.

Another approach for measuring mRNA abundance is RT-qPCR. In this technique, reverse transcription is followed by quantitative PCR. Reverse transcription first generates a DNA template from the mRNA; this single-stranded template is called cDNA. The cDNA template is then amplified in the quantitative step, during which the fluorescence emitted by labeled hybridization probes or intercalating dyes changes as the DNA amplification process progresses. With a carefully constructed standard curve, qPCR can produce an absolute measurement of the number of copies of original mRNA, typically in units of copies per nanolitre of homogenized tissue or copies per cell. qPCR is very sensitive (detection of a single mRNA molecule is theoretically possible).

For expression profiling, or high-throughput analysis of many genes within a sample, quantitative PCR may be performed for hundreds of genes simultaneously in the case of low-density arrays. A second approach is the hybridization microarray. A single array or "chip" may contain probes to determine transcript levels for every known gene in the genome of one or more organisms. Alternatively, "tag based" technologies like Serial analysis of gene expression (SAGE) and RNA-Seq, which can provide a relative measure of the cellular concentration of different mRNAs, can be used. An advantage of tag-based methods is the "open architecture", allowing for the exact measurement of any transcript, with a known or unknown sequence.

Next-generation sequencing (NGS) such as RNA-Seq is another approach, producing vast quantities of sequence data that can be matched to a reference genome. Although NGS is comparatively time-consuming, expensive, and resource-intensive, it can identify single-nucleotide polymorphisms, splice-variants, and novel genes, and can also be used to profile expression in organisms for which little or no sequence information is available. In some embodiments, nucleic acid sequencing methods are utilized for detection. Examples include, but are not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, the sequencing is automated sequencing. In some embodiments, the sequencing is parallel sequencing of partitioned amplicons (PCT Publication No: WO2006084132 to Kevin McKernan et al., herein incorporated by reference in its entirety). In some embodiments, the sequencing is DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

A variety of nucleic acid sequencing methods are contemplated for use in the methods of the present disclosure including, for example, chain terminator (Sanger) sequencing, dye terminator sequencing, and high-throughput sequencing methods. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

The present disclosure contemplates any method capable of receiving, processing, and transmitting the information to and from laboratories conducting the assays, information provides, medical personal, and subjects. For example, in some embodiments of the present disclosure, a sample (e.g., a biopsy or a blood or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may choose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action. In some embodiments, the results are used to select candidate therapies for drug screening or clinical trials.

In some embodiments, the results of the analysis are used to determine, recommend, or provide a diagnostic method. For example, if the gene expression profile is indicative of a MRI-visible tumor, the subject is offered MRI imaging as a first choice. If the gene expression profile is indicative of a tumor that is not MRI visible, the subject is offered an alternative diagnostic method. For example, in some embodiments, other imaging methods (e.g., ultrasound (e.g., transrectal ultrasound), bone scan, or CT scan) are offered. In some embodiments, a biopsy or surgical resection is offered.

Compositions for use in the methods described herein include, but are not limited to, kits comprising one or more reagents for determining the level of expression of genes described herein. In some embodiments, the reagents are, for example, a nucleic acid probe or probes that hybridizes to one or more genes described herein or one or more nucleic acid primers for the amplification or extension of the genes.

The probes may also be provided in the form of an array. In preferred embodiments, the kits contain all of the components necessary to perform a detection assay, including all controls, directions for performing assays, and any necessary software for analysis and presentation of results.

EXPERIMENTAL

The following examples are provided in order to demonstrate and further illustrate certain preferred embodiments and aspects of the present disclosure and are not to be construed as limiting the scope thereof.

Example 1

Methods

Study Design

The study used three independent patient populations: discovery, validation, and testing cohorts. First, patients with clinically localized disease who underwent preoperative mpMRI at the University of Michigan and were subsequently found to harbor multifocal PCa at RP were identified. The cohort was enriched for patients with both mpMRI visible and invisible PCa (FIGS. 1A and 1B) to constitute the discovery cohort. The validation cohort from Cedars-Sinai Medical Center included patients with either mpMRI-visible or -invisible foci, as previously described. 19 The testing cohort was composed of patients from the Decipher GRID PCa database treated at Johns Hopkins Medical Institute and Mayo Clinic who underwent genome-wide expression profiling after RP. 20,21

Preoperative Prostate mpMRI and Pathologic Evaluation

In the discovery and validation cohorts, mpMRI comprising T2-weighted imaging, diffusion-weighted imaging, and dynamic contrast-enhanced imaging was obtained. All mpMRI results were re-reviewed and coregistered with whole-mount formalin-fixed paraffin-embedded RP specimens to delineate mpMRI-visible (Prostate Imaging and Reporting Data System [PI-RADS] version 2; score, 3 to 5) and -invisible foci. Data on mpMRI were not available for the testing cohort. 22

Targeted DNA and RNA NGS

In the discovery cohort, DNA and RNA from each focus were co-isolated for targeted multiplex NGS as previously described. The targeted NGS assays were designed to assess relevant PCa genomic and transcriptomic alterations and derive clinically available prognostic tests. 15 The details of RNA sequencing in the validation cohort and genome-wide expression profiling in the testing cohorts have been previously described. 19,24

Bioinformatic Analysis of the Discovery Cohort

NGS data analysis was performed using Torrent Suite (4.2.0; Thermo Fisher Scientfic, Waltham, MA) and the Coverage Analysis Plug-ins v.5.0.4. (Thermo Fisher Scientific), along with the Ion Reporter (4.2.0; Thermo Fisher Scientific). All other analyses were performed using R Project for Statistical Computing v.3.2.3. Details regarding targeted NGS techniques, quality control parameters, DNA copy number alterations and variant calls, fusion isoform and partner level analysis, androgen receptor (AR) and ARsplice variants detection, and prognostic scores derivation have been previously described. 15, 25, 26 RNA target read counts were obtained using Torrent Suites RNA Coverage Analysis plugin, and total end to end reads for each target was calculated. Amplicons with zero counts or with inconsistent expression pattern were excluded from the analysis. Samples with less than 500,000 total mapped reads and/or less than 60% end to end reads were removed from analysis. Normalized expression values for each target were obtained by dividing log 2(read count+1) by samples mean log 2 housekeeping counts. ATPSE, ARF1, CLTC, and PGK1 were used as housekeeping targets 5, 8. Fusion status was calculated using only isoforms with at least 1000 reads across the cohort. Read counts of each isoform were summed, and samples with at least 500 reads for a given fusion pair and with log 2(pair+1)/log 2(housekeeping) >0.01 were deemed fusion positive.

Differential Gene Expression Analysis of mpMRI-Visible and -Invisible Cancer Foci To determine gene expression differences between mpMRI-visible and -invisible tumors, RNAseq data from the discovery cohort was analyzed using two approaches— differential expression (DE) analysis and random forest (RF) classifier. From these two approaches, a gene expression signature comprising independent differentially expressed genes was developed to predict mpMRI tumor visibility status. The model (i.e. the gene expression signature) was trained using a mixing alpha parameter of 0.1, and 3-fold cross validation optimizing for classification rate 9. The pROC R package v1.12.1 was used to construct a receiver operating characteristic (ROC) curve and calculate area under curve (AUC) for the gene expression signature using 2000 stratified bootstrapped sets of performance statistics to determine an optimal cut-off point for the gene expression signature. The CSMC cohort (n=16 samples; GSE95369) genome-wide expression profiling contained 25,702 genes. In order to validate the discovery UM gene expression signature in the CSMC validation cohort, the analytical data was limited to the genes included in the targeted RNA NGS panel (306 transcripts) used in the discovery cohort. The same pre-processing steps (data transformation, filtering, normalization using the same housekeeping genes) employed in the discovery cohort to were employed to generate the validation dataset from the CSMC cohort. The novel gene expression signature was then validated in the CSMC cohort, using the predetermined optimal probability cut-off (from the discovery cohort) to predict mpMRI visibility status.

Prognostic Significance of mpMRI-Based Gene Expression Signature

A total of 375 patients with genome-wide expression profiles were pooled from two independent case-cohort studies 20, 21 to constitute the testing cohort. The mpMRI-based nine-gene expression signature was applied to the testing cohort to predict mpMRI visibility status. Kaplan-Meier curves and Cox proportional hazard regression were used to evaluate the performance of this signature in predicting oncological outcomes: biochemical recurrence free survival (BFS), distant metastasis-free survival (DMFS), and PCa-specific mortality (PCSM). Multivariable analyses were performed to evaluate this signature as an independent predictor of oncological outcomes after adjusting for relevant clinicopathological variables, including preoperative prostate-specific antigen, pathologic grade group (GG), surgical margins, extraprostatic extension, seminal vesicle invasion, and lymph node invasion.

Spearman correlation analysis was performed to measure the association of the gene signature with cellular organization pathway activity. Mean expression of genes involved in the cellular organization pathway on the Oncotype Dx genomic prostate score (GPS; Genomic Health, Redwood City, CA) assay was correlated with the mpMRT-based gene expression signature. 27 Statistical analyses were performed in R version 3.3.3, and all statistical tests were two-sided using a 0.05 significance level.

Results

Study Cohorts

The discovery cohort included 10 patients from the University of Michigan PCa database with both mpMRI-visible and -invisible lesions (FIG. 1). Of the 26 cancer foci identified on surgical pathology specimens, 12 foci (46%) were visible on mpMRI. Among the 14 mpMRI-invisible foci (54%), five (36%) were GG2 and the remainder were GG1 (FIG. 1C). There were 16 patients in the validation cohort, of whom eight (50%) had mpMRI-invisible cancer lesions, and two of these (25%) were GG2. The median age at RP was 62 years, and median follow-up time for censored patients was 8 years. During follow-up, 136 (36.3%) patients experienced biochemical recurrence, 55 (14.7%) developed metastasis, and 28 (7.5%) died as a result of PCa.

Detection of Mutations and Copy Number Alterations in the Discovery Cohort

High-confidence mutations were detected in 14 of 26 (54%) tumor foci; six (43%) of the mutations were identified in mpMRT-invisible lesions. Notable somatic point mutations were in APC, ARID1B, ATM, NOTCH1, and SPOP. PTEN one copy number loss was detected in 25% (three of 12) and 14.3% (two of 14) of mpMRI-visible and -invisible foci, respectively (FIG. 1C).

Figure 2:
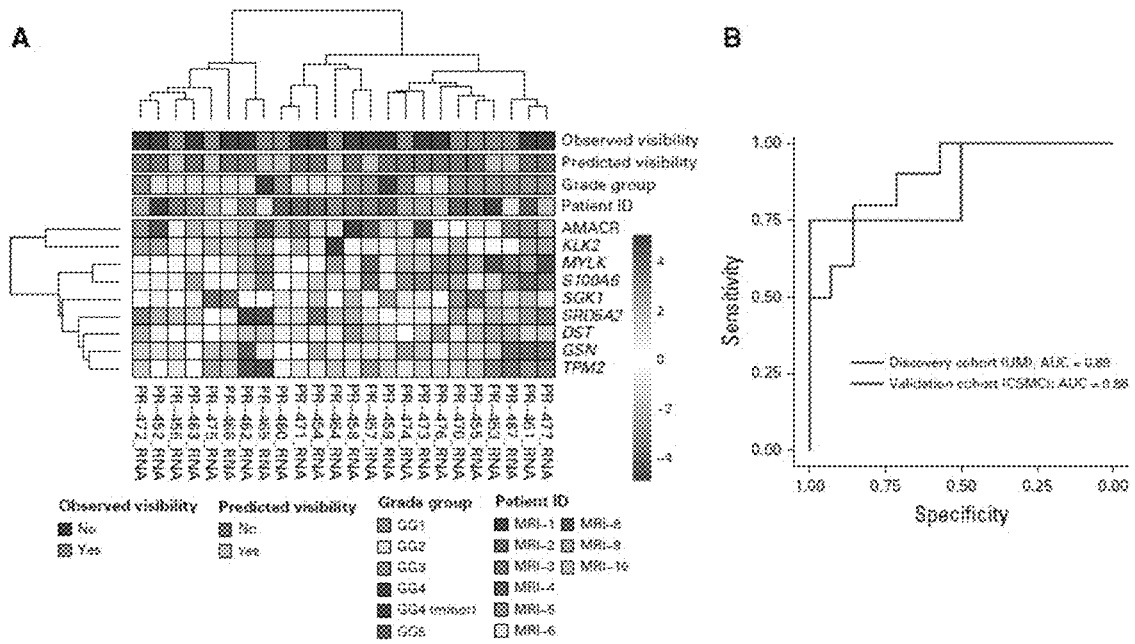
FIG. 2 shows development and validation of a nine-gene signature to predict multiparametric magnetic resonance imaging (mpMRI)-visible tumors. (A) Annotated heat map of differentially expressed genes in the training cohort. Comparisons of observed (first row) versus predicted (second row) mpMRI visibility using the nine-gene signature are shown in the annotation, as well as International Society of Urological Pathology grade group. (B) Receiver operating characteristic curves for the signature in the discovery (University of Michigan [UM]) versus the validation (Cedars-Sinai Medical Center [CSMC]) cohorts.

Discovery and Validation of a Nine-Gene Expression Signature for mpMRT Visibility Of the 26 total tumor foci in the discovery cohort and 306 amplicons on the RNAseq panel, 24 samples and 74 amplicons, respectively, passed quality control parameters and underwent DE analysis. Using DE analysis and RF classifier to identify candidate differentially expressed genes, four separate logistic regression models for predicting mpMRT tumor visibility status were interrogated using the 19 DE analysis genes, 20 RF genes, 11 shared genes between the DE analysis and RF gene sets, and 11 shared genes combined with the mutually exclusive genes. A multivariable RNAseq-based logistic regression model with the best performance for predicting mpMRI visibility status, comprising a nine-gene expression signature, was developed from the intersection of the DE analysis and RF gene sets (FIG. 2A). This signature correctly predicted seven (70%) of the mpMRI visible and 13 (93%) of the mpMRI-invisible foci in the discovery cohort, yielding an area under the curve of 0.89. The optimal probability cutoff for predicting mpMRI-visible tumor was greater than 0.46, with a sensitivity and specificity of 80% and 86%, respectively, in the discovery cohort (FIGS. 2A and 2B). Underexpression of seven of the nine genes in mpMRI-visible tumors was observed; the majority of which were stromal, cellular organization, and structure genes (FIG. 2A). The nine-gene expression signature was then evaluated in the independent validation cohort (Cedars-Sinai Medical Center) using the predetermined optimal probability cutoff (from the discovery cohort) to predict mpMRI visibility status. The receiver operating characteristic curve in the validation cohort is shown in FIG. 2B, with an area under the curve of 0.88. The sensitivity and specificity of the signature for predicting mpMRI visibility status were 75% and 100%, respectively, in the validation cohort. Notably, the signature correctly predicted two GG2 cancers that were mpMRI invisible in the validation cohort.

Prognostic Significance of the Nine-Gene mpMRI Visibility Expression Signature

Figure 3:
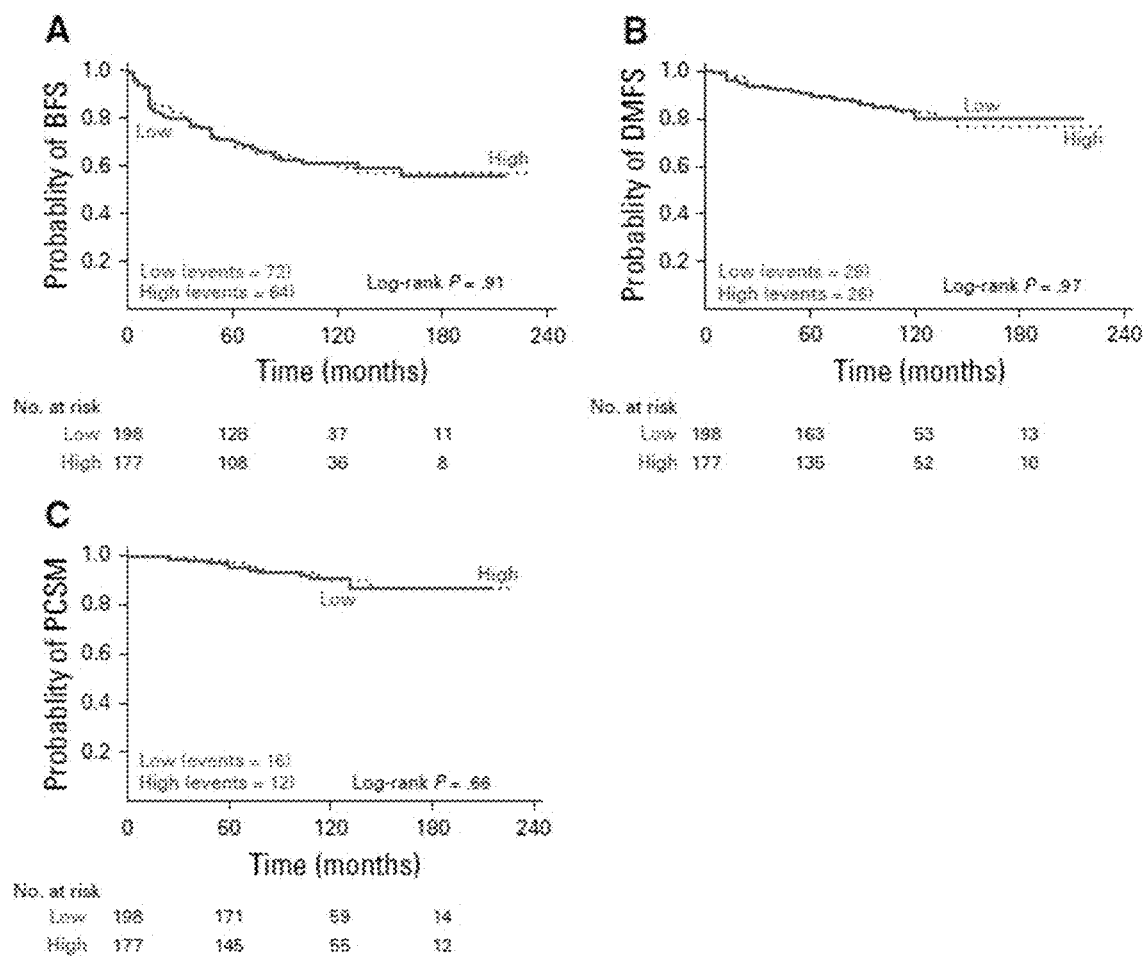
FIG. 3 shows the prognostic significance of predicted multiparametric magnetic resonance imaging (mpMRI) visibility status. Patients (n=375) in the testing cohort were pooled from two independent case-cohort studies (Johns Hopkins Medical Institute [n=260] and Mayo Clinic [n=235]) to test the capacity of predicted mpMRI visibility status to predict (A) biochemical recurrence-free survival (BFS), (B) distant metastasis-free survival (DMFS), and (C) prostate cancer-specific mortality (PCSM).
Figure 4:
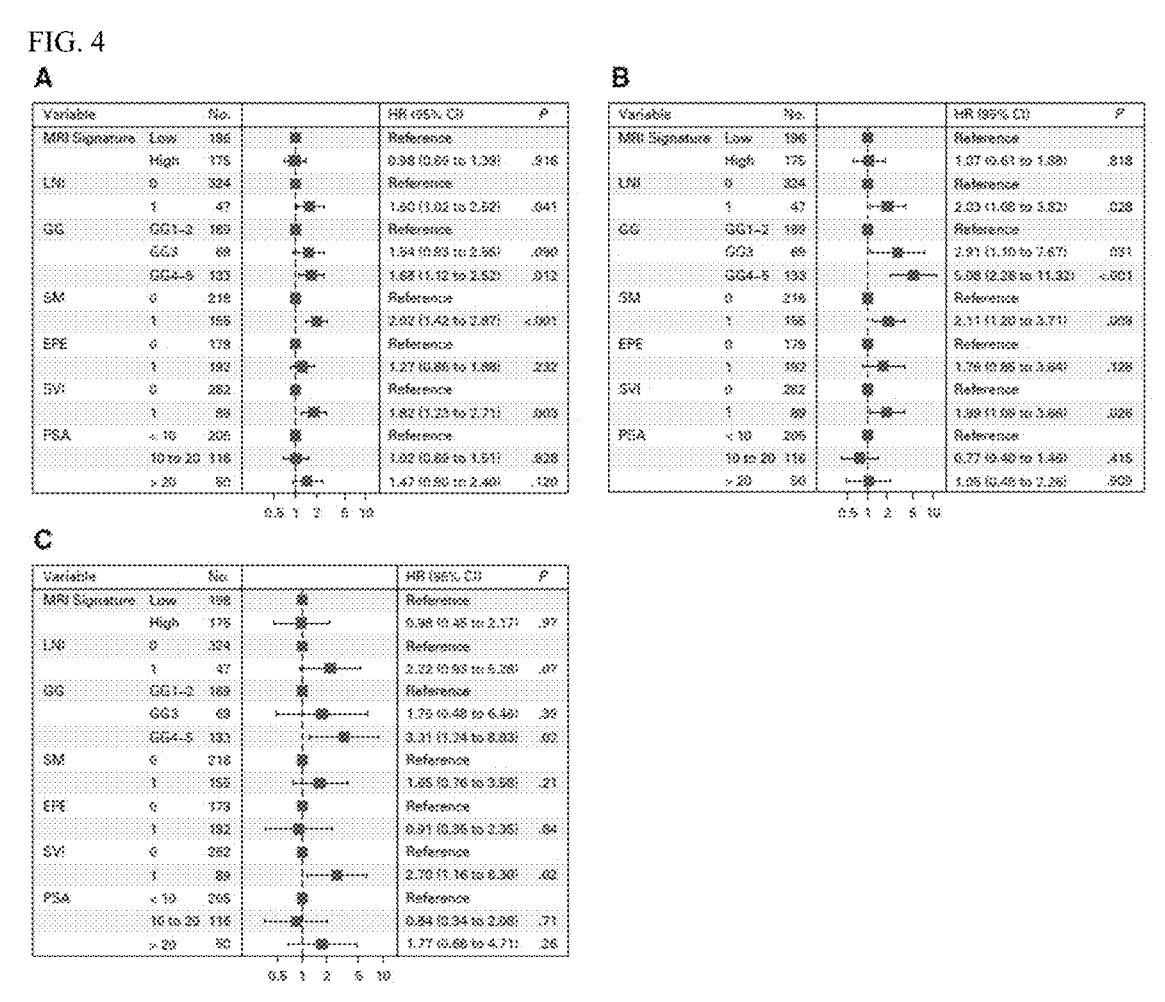

The distribution of each gene composing the nine-gene signature in the normalized microarray data (testing cohort) from the Decipher GRID mapped to The Cancer Genome Atlas Prostate Adenocarcinoma (TCGA-PRAD) RNAseq closely resemble that of the discovery cohort. The expression signature was applied to the testing cohort as a proxy for mpMRI tumor visibility. Of the 375 patients in the testing cohort, 177 (47.2%) were classified as mpMRI visible. Using the predicted probability as a surrogate for mpMRI, it was found that the mpMRI visibility signature was not a predictor of BFS, DMFS, or PCSM (FIG. 3; all log-rank P>0.05). Similar findings were observed when the testing cohort data were not mapped to the TCGA-PRAD RNAseq cohort (all log-rank P>0.05). Adjusting for relevant clinicopathological variables on multivariable analysis, it was found that genomic signature-determined mpMRI visibility status was not an independent predictor of BCR, metastasis, or PCSM (FIG. 4; all P>05). Similar findings were observed when the testing cohort data were not mapped to the TCGA-PRAD RNAseq data (Data Supplement; all P>0.05)

Molecular Basis of Cancer Visibility on mpMRI

Figure 5:
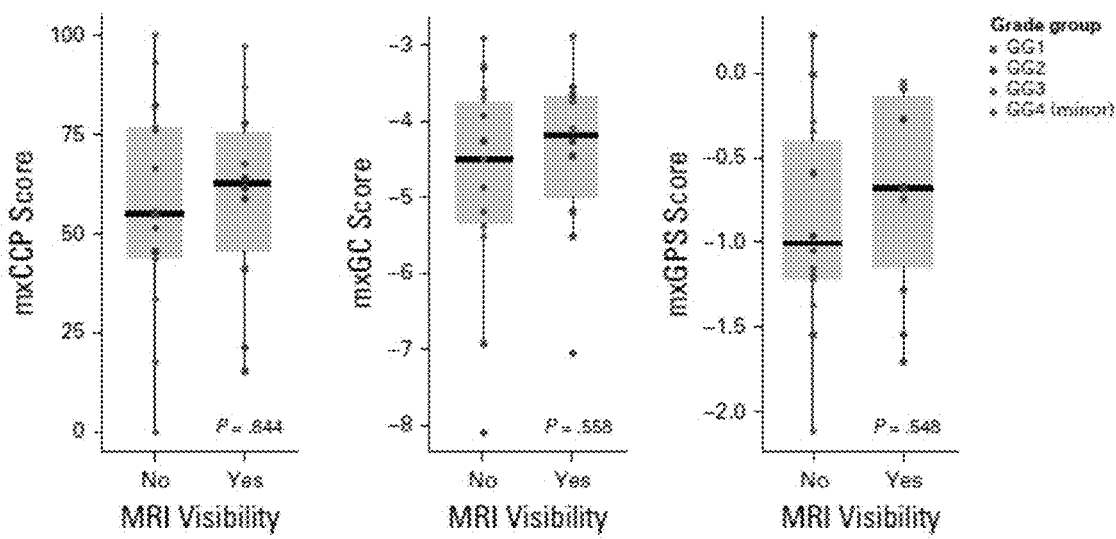
FIG. 5 shows derivation and comparison of expression-based prognostic scores between multiparametric magnetic resonance imaging (mpMRI)-visible and -invisible lesions. (A) Box plots of derived Prolaris cell cycle progression (mxCCP) score, Oncotype DX genomic prostate score (mxGPS), and Decipher genomic classifier (mxGC) stratified by mpMRI visibility status in the discovery cohort (n=10 patients; 26 cancer foci). (B) Comparisons of derived mxGPS submodules stratified by mpMRI visibility status.
Figure 5:
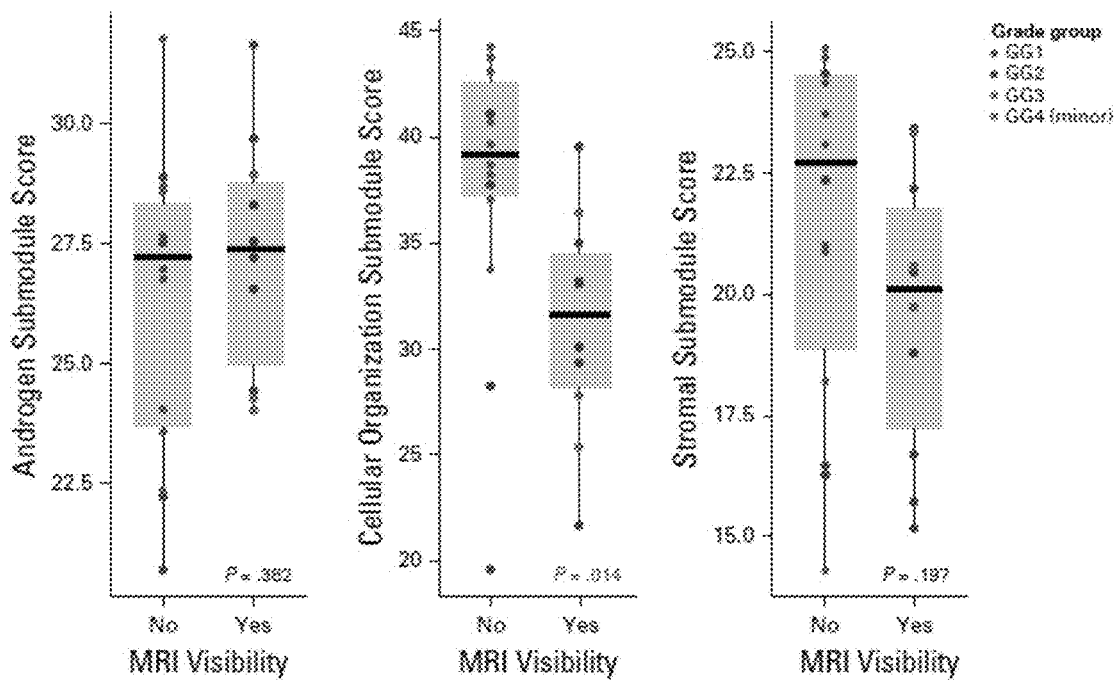

Using the multiplex (mx) RNAseq data from the discovery cohort, commercially available tissue-based prognostic biomarker test scores (Myriad Prolaris cell cycle progression [mxCCP] score, Oncotype DX [mxGPS], and the GenomeDX genomic classifier [mxGC]) were determined for each cancer focus, as previously described. 15 No significant difference in the mxCCP, mxGPS, and mxGC scores were found between mpMRI-visible and -invisible foci (FIG. 5A; all P>0.05). However, as described above, underexpression of seven of the nine genes in mpMRI visible tumors was observed, the majority of which were stromal, cellular organization, and structure genes (FIG. 2A).

Three subcomponents of the OncotypeDx GPS were computed, as previously described,15, 27 and these were compared between mpMRI-visible and -invisible tumors. There were no significant differences in the expression of OncotypeDx GPS androgen signaling and stromal response submodules between mpMRI-visible and -invisible tumors (FIG. 5B; both P>0.05). However, underexpression of the cellular organization submodule of the OncotypeDx GPS panel was found in mpMRI-visible tumors consistent with the results of the nine-gene signature (FIG. 5B; all P=0.014). Similarly, using data from the testing cohort, underexpression of the OncotypeDx GPS cellular organization module was found in predicted mpMRI-visible compared with -invisible foci (all P>0.05). Taken together, these findings support that loss of cellular organization and structure contributes to PCa visibility on mpMRI.

Gene Fusions and Gene Expression Analysis in the Discovery Cohort

Figure 6:
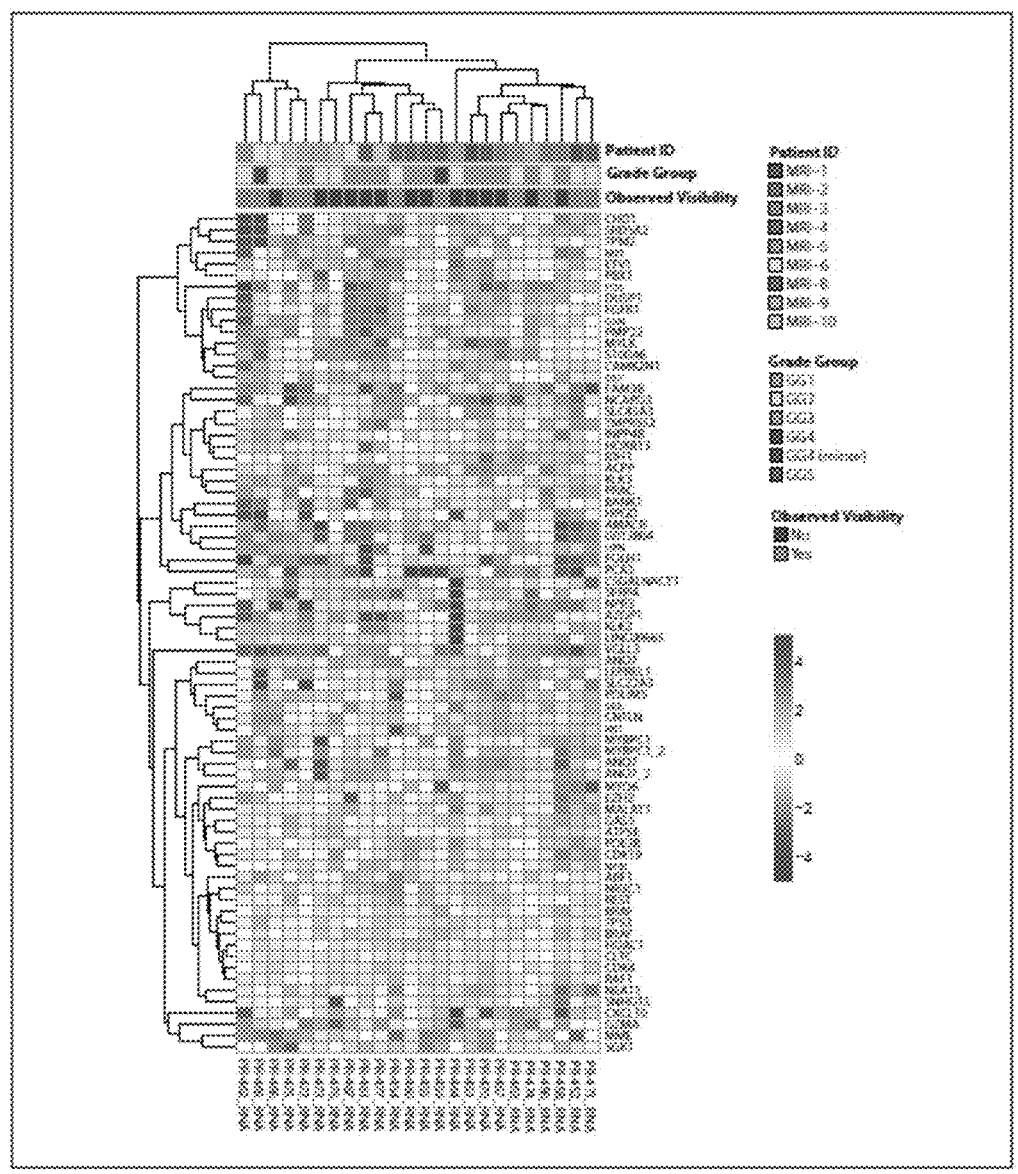
FIG. 6 shows RNA next generation sequencing of mpMRI visible and invisible lesions.
Figure 7:
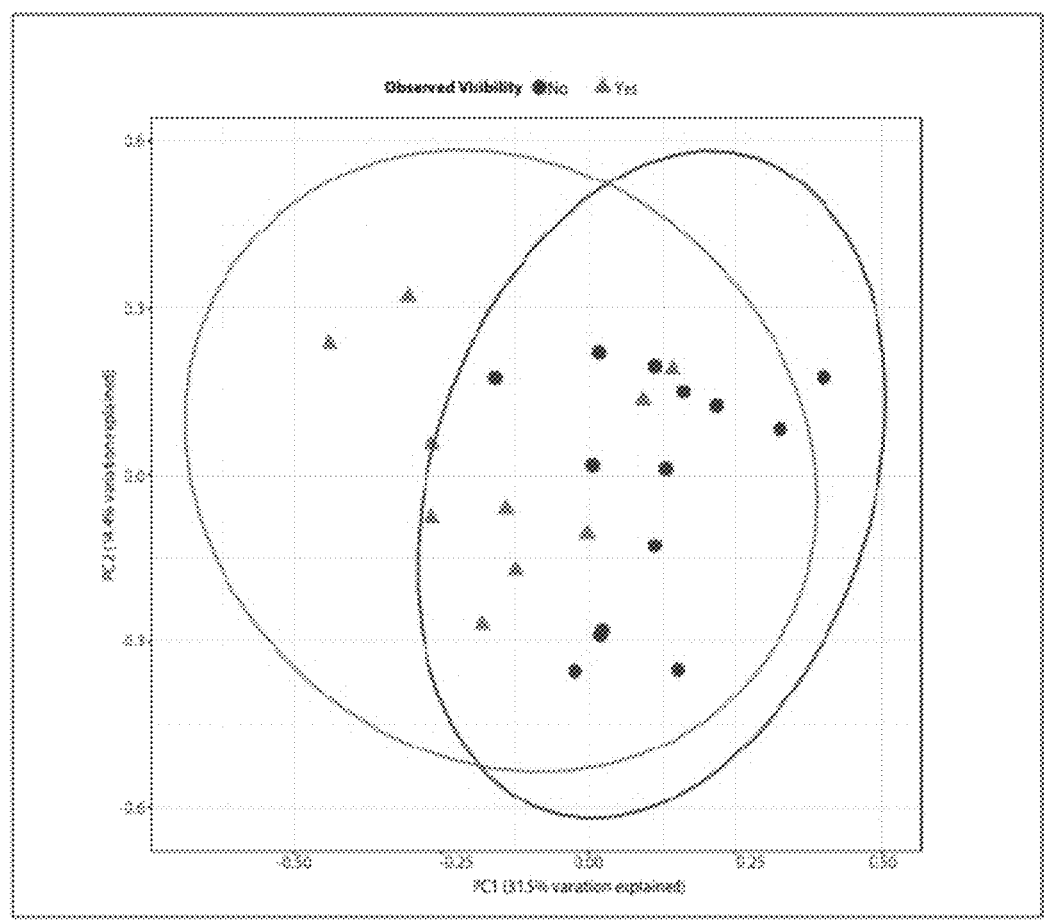
FIG. 7 shows Principle Component Analysis (PCA) of mpMRI visible and invisible prostate cancer.
Figure 8:
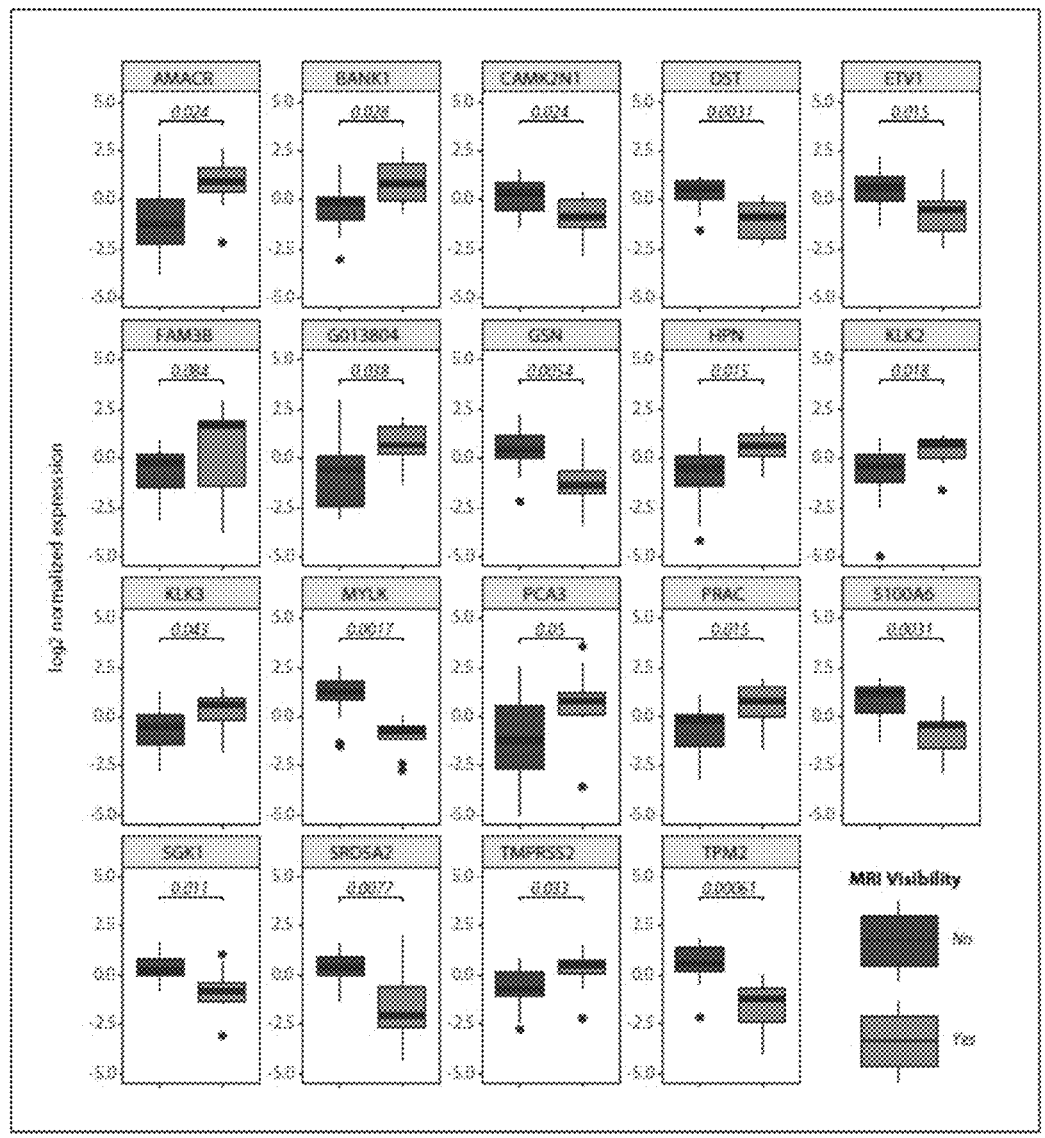
FIG. 8 shows EdgeR differential expression analysis to identify differentially expressed genes between mpMRI visible and invisible cancer foci.
Figure 9:
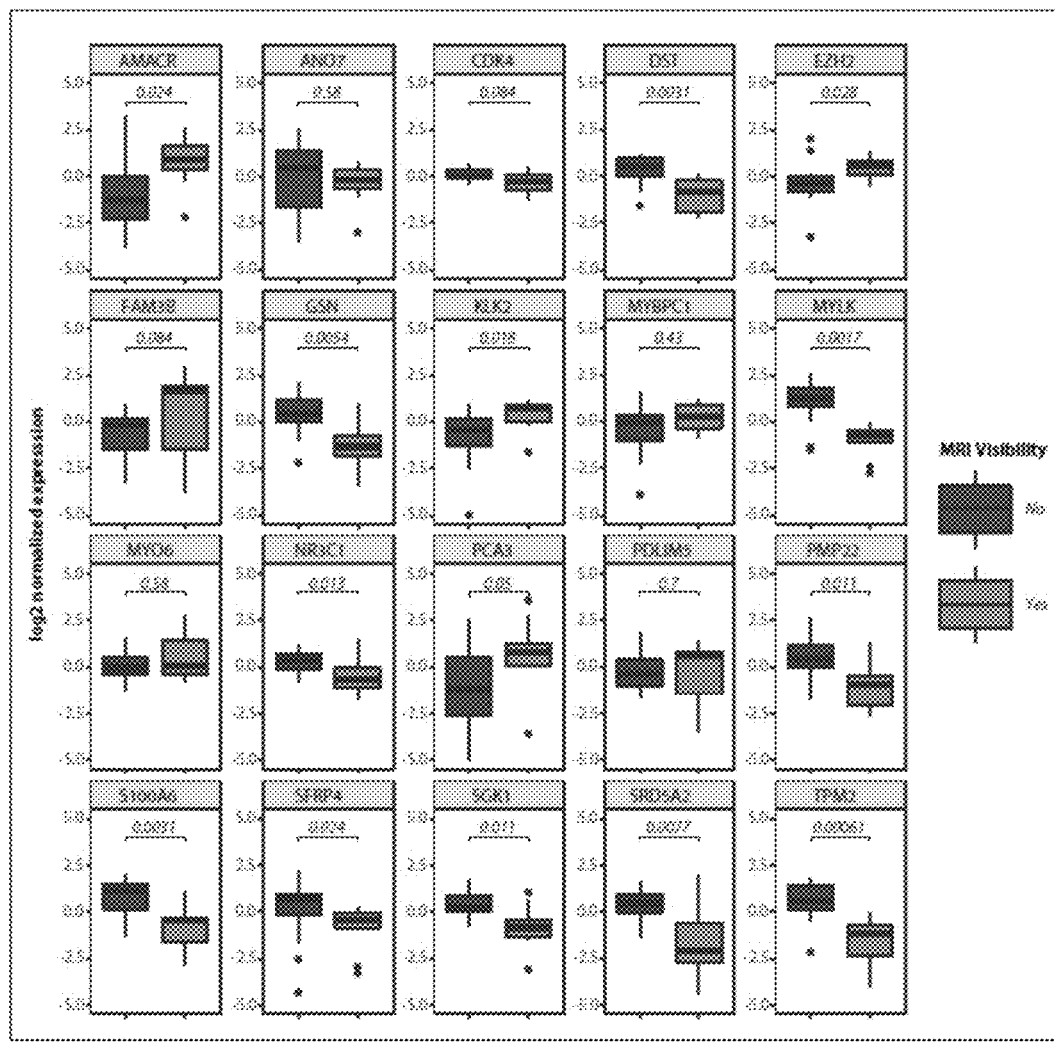
FIG. 9 shows Random Forest (RF) classifier to identify differentially expressed genes between mpMRI visible and invisible cancer foci.
Figure 10:
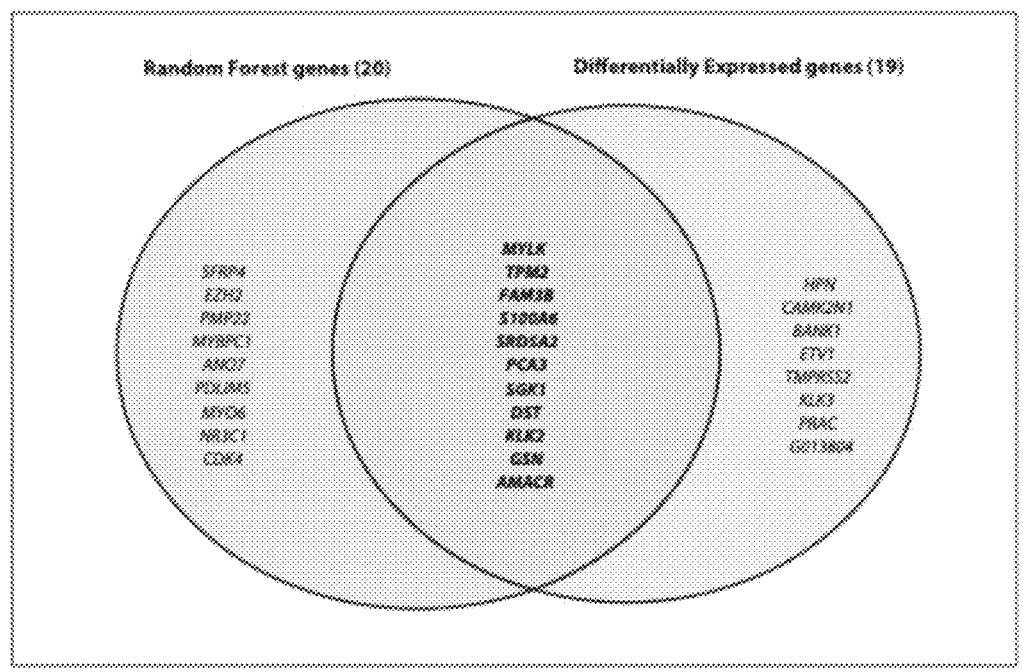
FIG. 10 shows differentially expressed genes between mpMRI visible and invisible cancer foci.
Figure 11:
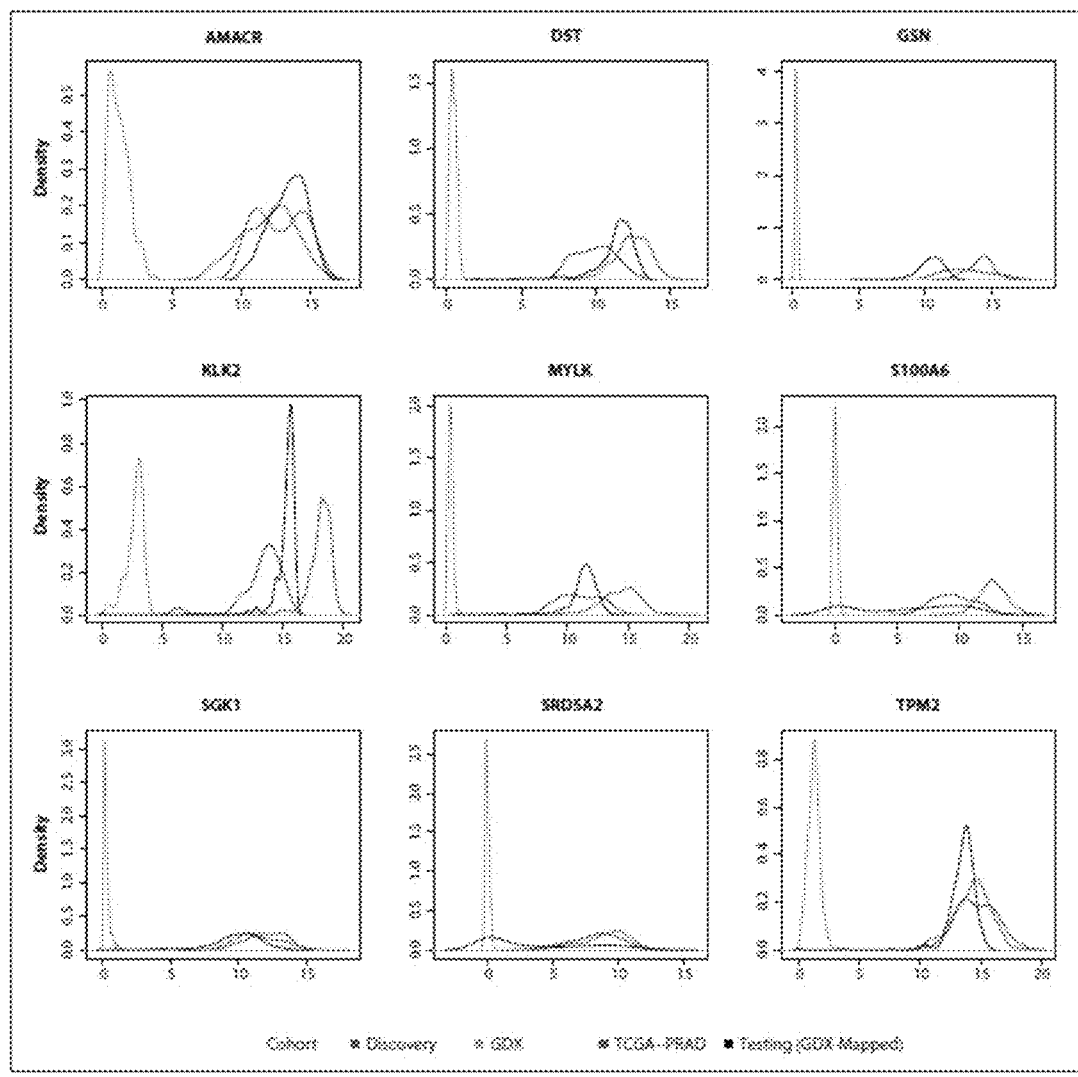
FIG. 11 shows transformation of Affymetrix microarrays data to RNAseq data in the testing cohort.
Figure 12:
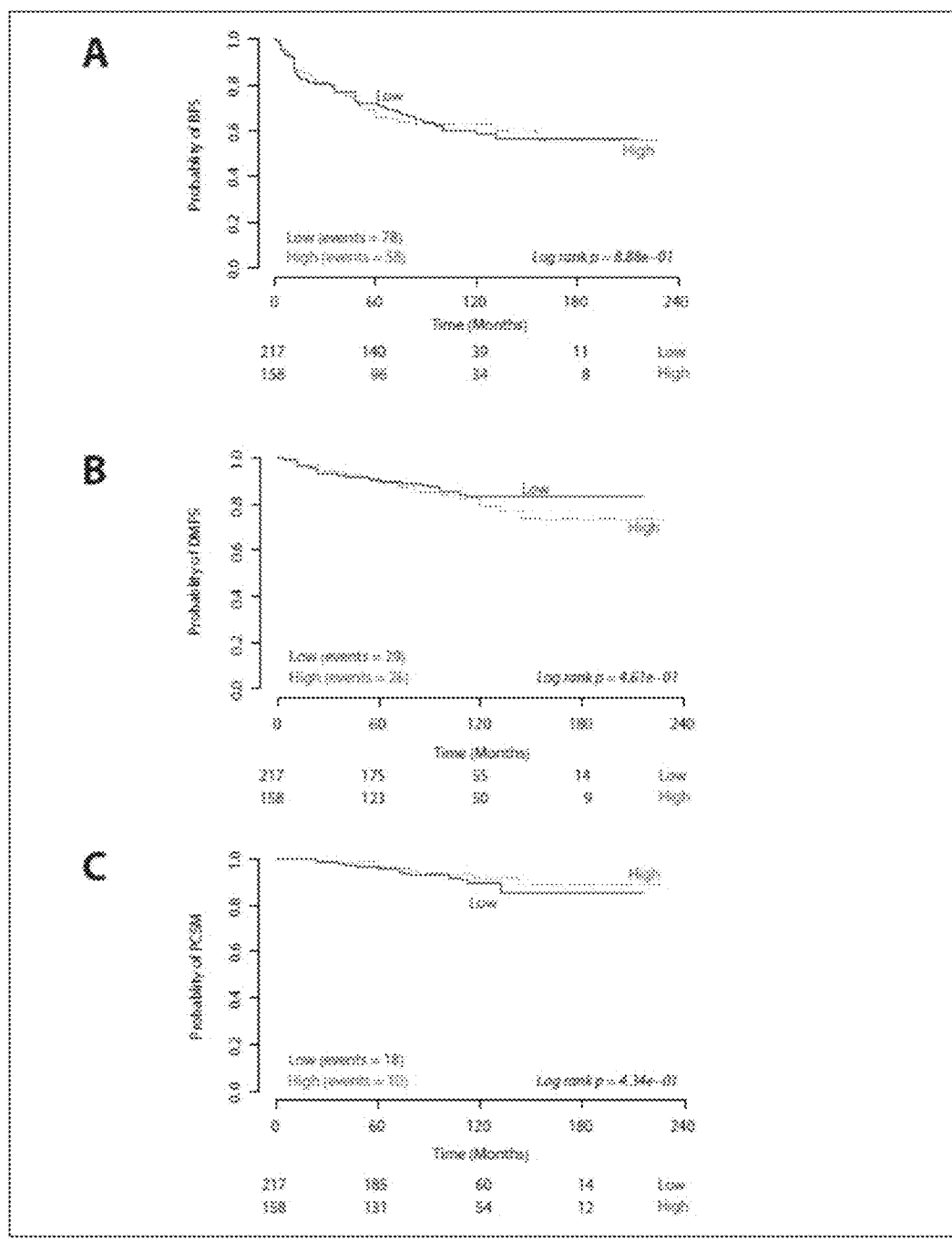
FIG. 12 shows prognostic significance of predicted mpMRI visibility status. Patients in the testing cohort (n=375) were pooled from two independent case-cohort studies [Johns Hopkins Medical Institution (n=260) and Mayo Clinic (n=235)] to test the capacity of predicted mpMRI visibility status to predict A). Biochemical recurrence free survival (BFS), B). Distant metastasis free survival (DMFS), and C). Prostate cancer specific mortality (PCSM).
Figure 13:
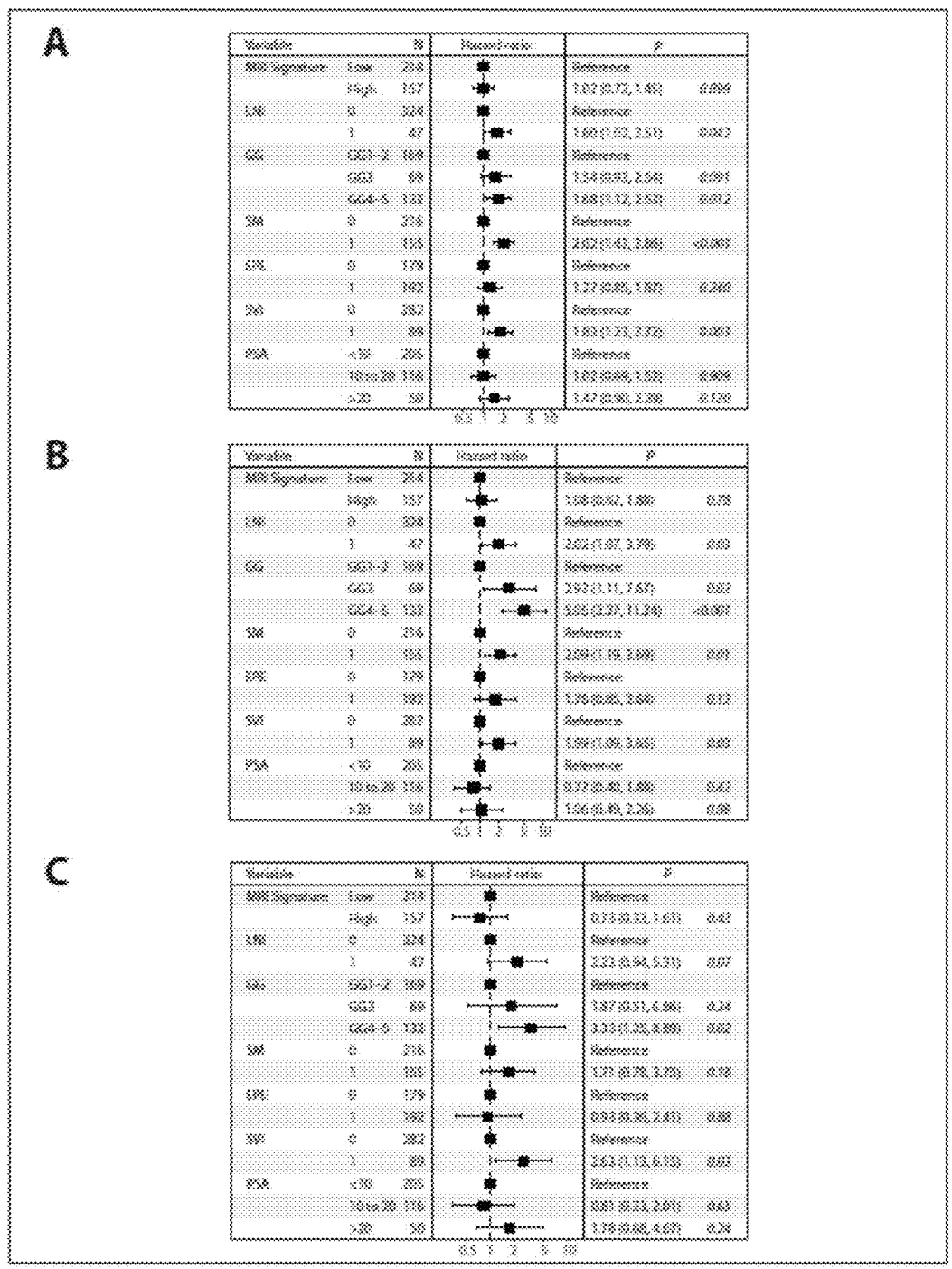
FIG. 13 shows multivariable analysis to assess the prognostic significance of predicted mpMRI visibility status. Using data from the testing cohort described in FIG. 12, multivariable Cox-proportional hazard models were developed to assess the capacity of predicted mpMRI visibility status to predict A). Biochemical recurrence free survival (BFS), B). Distant metastasis free survival (DMFS), and C). Prostate cancer specific mortality (PCSM), adjusting for relevant clinicopathological variables.
Figure 14:
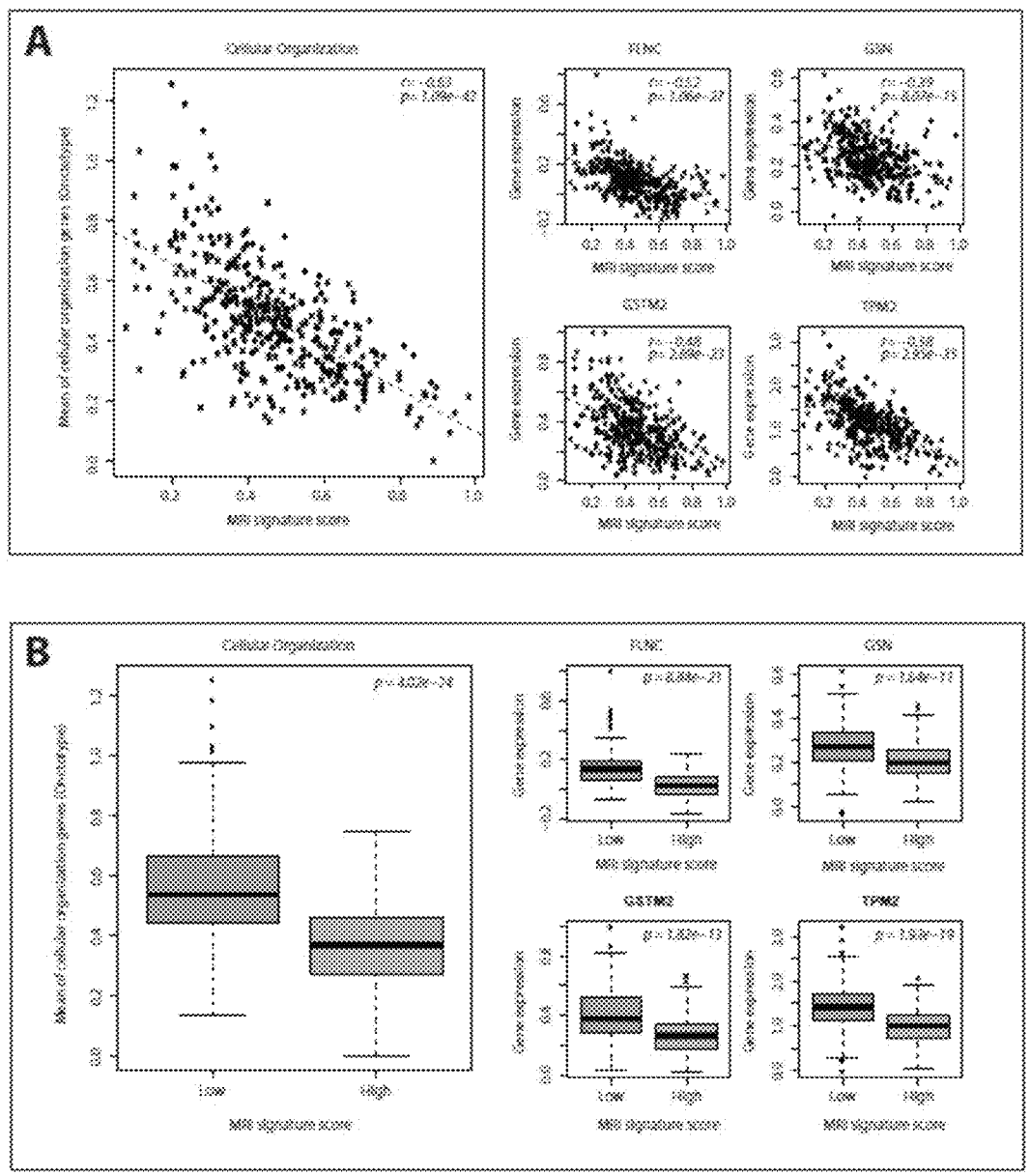
FIG. 14 shows interrogation of the molecular basis for predicted cancer visibility on mpMRI. A). There is an inverse correlation of the mean expression of both the composite and individual cellular organization genes with mpMRI visible signature score as a continuous variable (all p>0.05). B). Patients with high signature scores (>0.46; i.e. predicted mpMRI visible tumor) had lower mean expression of both the composite and individual cellular organization genes compared with patients with low signature scores (≤0.46; i.e. predicted mpMRI invisible tumor; all p>0.05).

Only two cancer foci (one each of mpMRI visible and invisible) from two different patients (Patients 4 and 8) demonstrated TMPRSS2:ERG gene fusions with concordant ERG expression (FIG. 1C). In these two patients, the other coexisting cancer foci did not harbor TMPRSS2:ERG gene fusion or demonstrate ERG expression, and they showed distinct PTEN one copy number losses and DNA variants. These findings support different clonal origins between each of these foci and co-existing lesions (FIG. 1C). Unsupervised hierarchical clustering of differentially expressed genes from the cohort of FFPE samples representing mpMRI visible and invisible cancer foci (n=26) is shown in FIG. 6. Principal components analysis using the 74 retained amplicons revealed that mpMRI visibility status accounted for 31.5% of the variation between visible and invisible samples indicating that mpMRI visibility status does not explain the majority of clustering of tumor foci (FIG. 7). DE analysis was performed with edgeR using the normalized RNAseq expression data from the discovery cohort and identified 19 differentially expressed genes between mpMRI visible and invisible tumors (FIG. 8). In parallel, the RF classifier was employed to identify 20 differentially expressed genes between mpMRI visible and invisible cancer foci (FIG. 10).

TABLE 1

Demographic, Clinicopathologic, and Imaging Characteristics of the Discovery Cohort (N = 10 patients; 26 Tumor foci)

| Patient ID | Age (Years) | PSA (ng/mL) | Overall Stage | # Primary tumor foci | # Invisible lesions | Grade Group (GG) mpMRI visible | Grade Group (GG) mpMRI invisible |
|---|---|---|---|---|---|---|---|
| 01 | 54 | 4.6 | pT2b | 2 | 1 | 2 (4; 2.0 cm) | 1 (0.3 cm) |
| 02 | 65 | 11.7 | pT2b | 2 | 1 | 2 (4; 0.8 cm) | 1 (0.5 cm) |
| 03 | 66 | 10.4 | pT2a+ | 3 | 2 | 2 (4; 1.3 cm) | 1 (0.6 cm) |
| 04 | 54 | 17.1 | pT3bN1 | 3 | 2 | 3 (4; 1.6 cm) | 1 (1.0 cm) |
| 05 | 65 | 5.6 | pT3a | 3 | 1 | 3 (5; 1.9 cm) | 2 (1.6 cm) |
| 06 | 57 | 9.8 | pT2b | 3 | 2 | 4 (4; 2.3 cm)* | 2 (1.3 cm) |
| 07 | 72 | 16.6 | pT2b | 2 | 0 | 2 (4; 1.0 cm)* | N/A |
| 08 | 71 | 3.7 | pT2b | 2 | 1 | 2 (4; 1.9 cm) | 1 (0.3 cm) |
| 09 | 64 | 19.5 | pT2b | 3 | 2 | 3 (4; 2.2 cm) | 2 (0.6 cm) |
| 10 | 65 | 8.1 | pT2b+ | 3 | 2 | 2 (4; 2.3 cm) | 2 (0.5 cm) |

Abbreviation:
ID-Identity;
PSA-Prostate specific antigen;
*Gleason score was 4 + 3 with tertiary pattern 5, classified as GG4.
*GG of second lesion was 1; and mpMRI-Magnetic resonance imaging.
Numbers in parenthese indicate the PIRADS of mpMRI visible lesions where applicable and maximum diameter of cancer focus measured on H/E.

TABLE 2

Demographic, Clinicopathologic, and Imaging Characteristics of the Validation Cohort (N = 16 patients)

| Variable | | MRI Visible (n = 8) | MRI Invisible (n = 8) |
|---|---|---|---|
| Mean PSA (SD) | | 7.5 (4.8) | 5.3 (1.8) |
| Clinical Stage | T1c | 3 | 6 |
| | T2a | 2 | 1 |
| | T2b | 3 | 1 |
| Grade Group | 1 | 1 | 6 |
| | 2 | 2 | 2 |
| | 3 | 2 | 0 |
| | 5 | 3 | 0 |
| Pathologic Stage | pT2 | 3 | 8 |
| | pT3a | 2 | 0 |
| | pT3b | 3 | 0 |

Abbreviation: MRI—Magnetic resonance imaging; PSA—Prostate specific antigen; SD—Standard deviation

TABLE 3

Demographic and Clinicopathologic Characteristics of Testing Cohort (n = 375).

| MRI Signature Score (Predicted Visibility Status) | | Overall (n = 375) | Low ("Invisible") (n = 198) | High ("Visible") (n = 177) | P-value |
|---|---|---|---|---|---|
| Mean MRI Signature Scores (SD) | | 0.47 (0.17) | 0.34 (0.09) | 0.61 (0.12) | <0.001 |
| Mean Age (SD) | | 61.46 (7.02) | 61.18 (6.99) | 61.77 (7.06) | 0.415 |
| ISUP Grade Group, n (%) | GG1 | 18 (4.8) | 12 (6.1) | 6 (3.4) | 0.084 |
| | GG2 | 153 (40.9) | 80 (40.6) | 73 (41.2) | |
| | GG3 | 69 (18.4) | 27 (13.7) | 42 (23.7) | |
| | GG4 | 51 (13.6) | 29 (14.7) | 22 (12.4) | |
| | GG5 | 83 (22.2) | 49 (24.9) | 34 (19.2) | |
| SVI, n (%) | | 91 (24.3) | 53 (26.8) | 38 (21.5) | 0.283 |
| EPE, n (%) | | 192 (51.5) | 92 (46.5) | 100 (57.1) | 0.051 |
| Mean Pre-operative PSA (SD) | | 12.63 (13.92) | 12.02 (10.55) | 13.30 (16.92) | 0.374 |
| Pre-operative PSA, n (%) | <10 | 208 (55.5) | 103 (52.0) | 105 (59.3) | 0.147 |
| | 10-20 | 116 (30.9) | 70 (35.4) | 46 (26.0) | |
| | >20 | 51 (13.6) | 25 (12.6) | 26 (14.7) | |
| Positive Surgical Margin, n (%) | | 158 (42.1) | 79 (39.9) | 79 (44.6) | 0.411 |
| Lymph Node Involvement, n (%) | | 47 (12.6) | 26 (13.2) | 21 (11.9) | 0.816 |
| Androgen Deprivation Therapy, n (%) | | 113 (30.2) | 56 (28.4) | 57 (32.2) | 0.496 |
| Radiation Therapy, n (%) | | 73 (19.5) | 39 (19.8) | 34 (19.2) | 0.99 |
| Biochemical Recurrence, n (%) | | 136 (36.3) | 72 (36.4) | 64 (36.2) | 1 |
| Metastasis, n (%) | | 55 (14.7) | 29 (14.6) | 26 (14.7) | 1 |
| Prostate Cancer Specific Mortality, n (%) | | 28 (7.5) | 16 (8.1) | 12 (6.8) | 0.778 |
| Pathological Tumor Stage, n (%) | pT2a | 24 (6.5) | 17 (8.6) | 7 (4.0) | 0.013 |
| | pT2b | 64 (17.2) | 31 (15.7) | 33 (18.9) | |
| | pT2c | 50 (13.4) | 35 (17.8) | 15 (8.6) | |
| | pT2x | 5 (1.3) | 2 (1.0) | 3 (1.7) | |

TABLE 3-continued

Demographic and Clinicopathologic Characteristics of Testing Cohort (n = 375).

| MRI Signature Score (Predicted Visibility Status) | | Overall (n = 375) | Low ("Invisible") (n = 198) | High ("Visible") (n = 177) | P-value |
|---|---|---|---|---|---|
| | pT3a | 122 (32.8) | 53 (26.9) | 69 (39.4) | |
| | pT3b | 107 (28.8) | 59 (29.9) | 48 (27.4) | |

Abbreviation: ID—Identity; PSA—Prostate specific antigen.
*Gleason score was 4 + 3 with tertiary pattern 5, classified as GG4.
*GG of second lesion was 1; and
MRI—Magnetic resonance imaging.
Numbers in parentheses indicates PIRADS of MRI visible lesions.

TABLE 4

Nine-gene expression signature model equation for predicting multiparametric magnetic resonance imaging (mpMRI) visible prostate cancer. The model calculates the probability of a sample being classified as mpMRI visible:

$$P = \frac{e^{\beta_0 + \Sigma X_i B_i}}{1 + e^{\beta_0 + \Sigma X_i B_i}}$$

Where $X_i$ represents the genes expression, and $\beta_0$ represents the genes trained coefficients

| Equation Term | Coefficient |
|---|---|
| Intercept, $\beta_0$ | −0.1986805 |
| AMACR | 0.07847622 |
| DST | −0.1703643 |
| GSN | −0.0634344 |
| KLK2 | 0.10499332 |
| MYLK | −0.2498781 |
| S100A6 | −0.2451604 |
| SGK1 | −0.3260369 |
| SRD5A2 | −0.0938734 |
| TPM2 | −0.1517305 |

TABLE 5

Functional annotation of each gene comprising the 9-gene expression signature for predicting mpMRI visible prostate cancer. The significant (FDR < 5%) differentially expressed genes are listed with observed log2-fold change values, classifier groups, functions, and usage.

| Gene | Group | Usage | Log$_2$Fold Change | Function |
|---|---|---|---|---|
| AMACR | Subtyping: PCa vs. Normal | GenomeDX | 2.273615 | Conversion of pristanoyl-CoA and C27-bile acyl-Coas to their (S)-stereoisomers [14,15] |
| KLK2 | AR signaling | Oncotype DX | 1.287147 | Cleaves pro-PSA to PSA[16,17] |
| MYLK | Stroma | NA | −2.047631 | Encodes myosin light chain kinase, a $Ca^{2+}$/calmodulin dependent enzyme[18,19] |
| S100A6 | AR Signaling | NA | −1.483567 | Involved in cell cycle progression and differentiation[20] |
| SGK1 | Subtyping | NA | −1.006531 | Plays an important role in cellular stress response[21,22] |
| SRD5A2 | AR Signaling | Oncotype DX | −2.004192 | Involved in synthesis of DHT, sexual differentiation and androgen physiology[23,24] |
| DST | PCa vs. Normal | NA | −1.196103 | Cytoskeletal linker protein[25] |
| GSN | Cellular Organization; Stroma | OncotypeDX | −1.700414 | Regulates cell morphology, differentiation, movement, and apoptosis[26] |
| TPM2 | Cellular Organization | OncotypeDX | −2.077787 | Central role in the Ca2+ dependent regulation of muscle contraction[27,28] |

TABLE 6

Multivariable analysis to assess the prognostic significance of predicted mpMRI visibility status. The Affymetrix microarrays gene expression data was matched to The Cancer Genome Atlas prostate adenocarcinoma (TCGA-PRAD) RNAseq data to form the testing cohort (n = 375).

|  | BCR | | METS | | PCSM | |
| --- | --- | --- | --- | --- | --- | --- |
| Varible | HR | P-Value | HR | P-Value | HR | P-Value |
| mpMRI Signature | 0.98 (0.69, 1.39) | 0.92 | 1.07 (0.61, 1.88) | 0.62 | 0.98 (0.45, 2.17) | 0.97 |
| LNI | 1.60 (1.02, 2.52) | 0.04 | 2.03 (1.06, 3.82) | 0.03 | 2.22 (0.93, 5.28) | 0.07 |
| GG 3' | 1.54 (0.93, 2.55) | 0.09 | 2.91 (1.10, 7.67) | 0.03 | 1.76 (0.46, 6.46) | 0.39 |
| GG 4-5 | 1.66 (1.12, 2.52) | 0.01 | 5.08 (2.26, 11.32) | 0.00 | 3.31 (1.24, 8.63) | 0.02 |
| SMI | 2.02 (1.42, 2.87) | 0.00 | 2.11 (1.20, 3.71) | 0.01 | 1.65 (0.76, 3.58) | 0.21 |
| EPE | 1.27 (0.86, 1.88) | 0.23 | 1.76 (0.85, 3.64) | 0.13 | 0.91 (0.35, 2.35) | 0.84 |
| SVI | 1.82 (1.23, 2.71) | 0.00 | 1.99 (1.09, 3.66) | 0.03 | 2.70 (1.16, 6.30) | 0.02 |
| *PSA 10-20, ng/dL | 1.02 (0.69, 1.51) | 0.93 | 0.77 (0.40, 1.46) | 0.42 | 0.68 (0.34, 2.08) | 0.71 |
| *PSA > 20, ng/dL | 1.47 (0.90, 2.40) | 0.12 | 1.05 (0.48, 2.26) | 0.91 | 1.77 (0.66, 4.71) | 0.26 |

*GG 1-2 used as a reference category.
*Preoperative.
Abbreviations:
mpMRI-multiparametric magnetic resonance imaging;
LNI-lymph node invasion;
GG-grade group;
SM-seminal vesicle invasion;
EPE-extraprostatic extension;
SVI-seminal vesicle invasion; and
PSA-prostate specific antigen

TABLE 7

Multivariable analysis to assess the prognostic significance of predicted mpMRI visibility status. The Affymetrix microarrays gene expression data was not matched to The Cancer Genome Atlas prostate adenocarcinoma (TCGA-PRAD) RNAseq data in this exploratory analysis (n = 375).

|  | BCR | | METS | | PCSM | |
| --- | --- | --- | --- | --- | --- | --- |
| Varible | HR | P-Value | HR | P-Value | HR | P-Value |
| mpMRI Signature | 1.02 (0.72, 1.45) | 0.90 | 1.08 (0.62, 1.88) | 0.78 | 0.73 (0.33, 1.61) | 0.43 |
| LNI | 1.60 (1.02, 2.51) | 0.04 | 2.02 (1.07, 3.79) | 0.03 | 2.23 (0.94, 5.31) | 0.07 |
| GG 3' | 1.54 (0.93, 2.54) | 0.09 | 2.92 (1.11, 7.67) | 0.03 | 1.67 (0.51, 6.86) | 0.34 |
| GG 4-5 | 1.68 (1.12, 2.53) | 0.01 | 5.05 (2.27, 11.24) | 0.00 | 3.33 (1.25, 8.69) | 0.02 |
| SMI | 2.02 (1.42, 2.86) | 0.00 | 2.09 (1.19, 3.69) | 0.01 | 1.71 (0.78, 3.75) | 0.18 |
| EPE | 1.27 (0.65, 1.87) | 0.24 | 1.75 (0.65, 3.64) | 0.13 | 0.93 (0.36, 2.41) | 0.88 |
| SVI | 1.83 (1.23, 2.72) | 0.00 | 1.99 (1.09, 3.65) | 0.03 | 2.63 (1.13, 6.15) | 0.03 |
| *PSA 10-20, ng/dL | 1.02 (0.69, 1.52) | 0.91 | 0.77 (0.40, 1.48) | 0.43 | 0.81 (0.33, 2.01) | 0.65 |
| *PSA > 20, ng/dL | 1.47 (0.90, 2.39) | 0.12 | 1.06 (0.49, 2.26) | 0.88 | 1.78 (0.66, 4.67) | 0.24 |

*GG 1-2 used as a reference category.
*Preoperative.
Abbreviations:
mpMRI-multiparametric magnetic resonance imaging;
LNI-lymph node invasion;
GG-grade group;
SM-seminal vesicle invasion;
EPE-extraprostatic extension;
SVI-seminal vesicle invasion; and
PSA-prostate specific antigen Example 2

Figure 15:
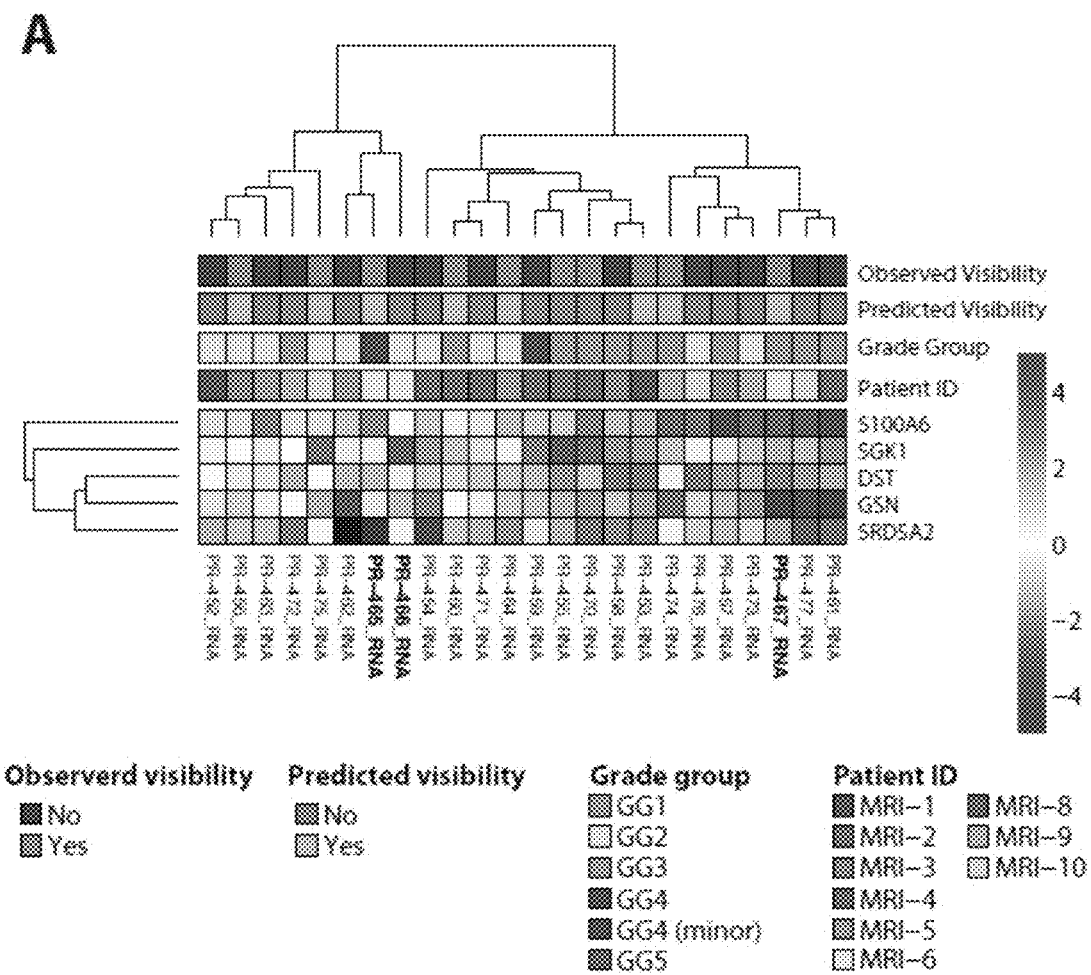
FIG. 15 shows development and validation of a five-gene signature to predict multiparametric magnetic resonance imaging (mpMRI)-visible tumors. (A) Annotated heat map of differentially expressed genes in the training cohort. (B) Receiver operating characteristic curves for the signature in the discovery (University of Michigan [UM]) versus the validation (Cedars-Sinai Medical Center [CSMC]) cohorts.
Figure 15:
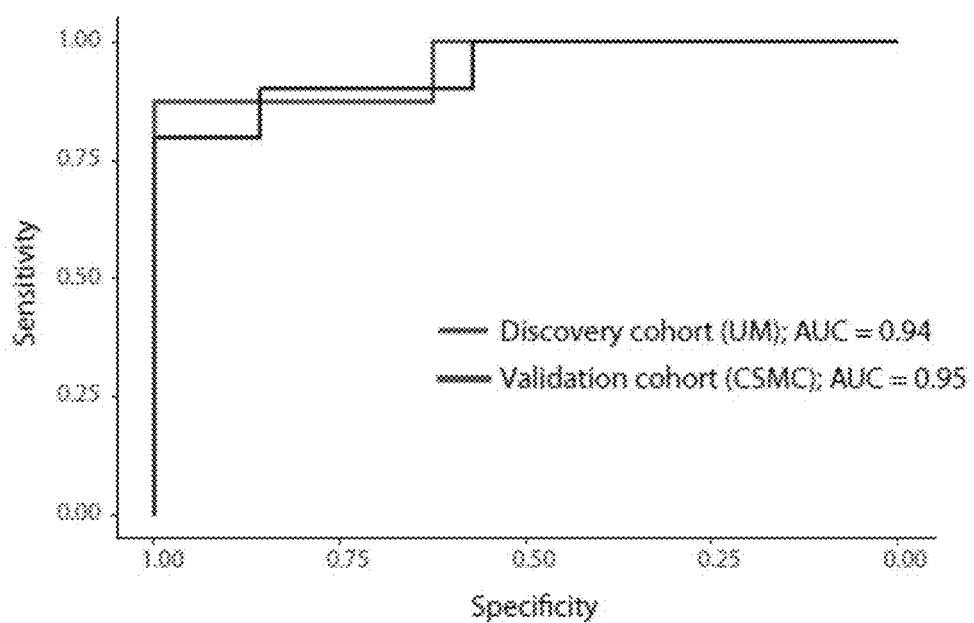

This Example described development and validation of a five-gene signature to predict multiparametric magnetic resonance imaging (mpMRI)-visible tumors. Results are shown in FIG. 15. FIG. 15S shows an annotated heat map of differentially expressed genes in the training cohort. Differentially expressed genes were identified with the EdgeR package using a Benjamini-Hochberg procedure adjusted false discovery rate cutoff of less than 0.05. Targets and samples were clustered using hierarchical clustering on the basis of Euclidian distances. Comparisons of observed (first row) versus predicted (second row) mpMRI visibility using the five-gene signature are shown in the annotation, as well as grade group. FIG. 15 B shows receiver operating characteristic curves for the signature in the discovery (University of Michigan [UM]) versus the validation (Cedars-Sinai Medical Center [CSMC]) cohorts. The signature was developed with multivariable ridge logistic-regression model using cross validation for λ hyperparameter selection. The area under the curve (AUC) for the signature was not significantly different between the discovery and the validation cohorts (0.94 v 0.95, Delong's unpaired t test, P=0.886). The optimal probability cutoff for predicting mpMRI-visible tumor was greater than 0.615, with a sensitivity and specificity of 88% and 88% in the validation cohort, respectively.

REFERENCES

1. Kasivisvanathan V, Rannikko A S, Borghi M, et al: MRI-targeted or standard biopsy for prostate-cancer diagnosis. N Engl J Med 378:1767-1777, 2018
2. Ahmed H U, El-Shater Bosaily A, Brown L C, et al: Diagnostic accuracy of multi-parametric MRI and TRUS biopsy in prostate cancer (PROMIS): A paired validating confirmatory study. Lancet 389:815-822, 2017
3. Filson C P, Natarajan S, Margolis D J A, et al: Prostate cancer detection with magnetic resonance-ultrasound fusion biopsy: The role of systematic and targeted biopsies. Cancer 122:884-892, 2016
4. Salami S S, Ben-Levi E, Yaskiv O, et al: In patients with a previous negative prostate biopsy and a suspicious lesion on magnetic resonance imaging, is a 12-core biopsy still necessary in addition to a targeted biopsy? BJU Int 115:562-570, 2015
5. Salami S S, Vira M A, Turkbey B, et al: Multiparametric magnetic resonance imaging outperforms the Prostate Cancer Prevention Trial risk calculator in predicting clinically significant prostate cancer. Cancer 120:2876-2882, 2014
6. Siddiqui M M, Rais-Bahrami S, Turkbey B, et al: Comparison of MR/ultrasound fusion-guided biopsy with ultrasound-guided biopsy for the diagnosis of prostate cancer. JAMA 313:390-397, 2015
7. Ahmed H U, Hindley R G, Dickinson L, et al: Focal therapy for localised unifocal and multifocal prostate cancer: A prospective development study. Lancet Oncol 13:622-632, 2012
8. Natarajan S, Raman S, Priester A M, et al: Focal laser ablation of prostate cancer: Phase I clinical trial. J Urol 196:68-75, 2016
9. Ahmed H U, Dickinson L, Charman S, et al: Focal ablation targeted to the index lesion in multifocal localised prostate cancer: A prospective development study. Eur Urol 68:927-936, 2015
10. Guillaumier S, Peters M, Arya M, et al: A multicentre study of 5-year outcomes following focal therapy in treating clinically significant nonmetastatic prostate cancer. Eur Urol 74:422-429, 2018
11. Boutros P C, Fraser M, Harding N J, et al: Spatial genomic heterogeneity within localized, multifocal prostate cancer. Nat Genet 47:736-745, 2015
12. Cooper C S, Eeles R, Wedge D C, et al: Analysis of the genetic phylogeny of multifocal prostate cancer identifies multiple independent clonal expansions in neoplastic and morphologically normal prostate tissue. Nat Genet 47:367-372, 2015 [Erratum: Nat Genet 47:689, 2015]
13. Cancer Genome Atlas Research Network: The molecular taxonomy of primary prostate cancer. Cell 163:1011-1025, 2015
14. Kumar A, Coleman I, Morrissey C, et al: Substantial interindividual and limited intraindividual genomic diversity among tumors from men with metastatic prostate cancer. Nat Med 22:369-378, 2016
15. Salami S S, Hovelson D H, Kaplan J B, et al: Transcriptomic heterogeneity in multifocal prostate cancer. JCI Insight 3:123468, 2018
16. Radtke J P, Kuru T H, Boxler S, et al. Comparative analysis of transperineal template saturation prostate biopsy versus magnetic resonance imaging targeted biopsy with magnetic resonance imaging-ultrasound fusion guidance. J Urol 193:87-94, 2015
17. Johnson D C, Raman S S, Mirak S A, et al: Detection of individual prostate cancer foci via multiparametric magnetic resonance imaging. Eur Urol 75:712-720, 2019
18. Parry M A, Srivastava S, Ali A, et al. Genomic evaluation of multiparametric magnetic resonance imaging-visible and -nonvisible lesions in clinically localised prostate cancer. Eur Urol Oncol 2:1-11, 2019
19. Li P, You S, Nguyen C, et al: Genes involved in prostate cancer progression determine MRI visibility. Theranostics 8:1752-1765, 2018
20. Ross A E, Johnson M H, Yousefi K, et al: Tissue-based genomics augments post-prostatectomy risk stratification in a natural history cohort of intermediate- and high-risk men. Eur Urol 69:157-165, 2016
21. Karnes R J, Bergstralh E J, Davicioni E, et al: Validation of a genomic classifier that predicts metastasis following radical prostatectomy in an at risk patient population. J Urol 190:2047-2053, 2013
22. Weinreb J C, Barentsz J O, Choyke P L, et al: PI-RADS Prostate Imaging-Reporting and Data System: 2015, Version 2. Eur Urol 69:16-40, 2016
23. Hovelson D H, McDaniel A S, Cani A K, et al: Development and validation of a scalable next-generation sequencing system for assessing relevant somatic variants in solid tumors. Neoplasia 17:385-399, 2015
24. Erho N, Crisan A, Vergara I A, et al: Discovery and validation of a prostate cancer genomic classifier that predicts early metastasis following radical prostatectomy. PLoS One 8:e66855, 2013
25. Warrick J I, Hovelson D H, Amin A, et al: Tumor evolution and progression in multifocal and paired non-invasive/invasive urothelial carcinoma. Virchows Arch 466:297-311, 2015
26. Palapattu G S, Salami S S, Cani A K, et al: Molecular profiling to determine clonality of serial magnetic resonance imaging/ultrasound fusion biopsies from men on active surveillance for low-risk prostate cancer. Clin Cancer Res 23:985-991, 2017
27. Klein E A, Cooperberg M R, Magi-Galluzzi C, et al: A 17-gene assay to predict prostate cancer aggressiveness in the context of Gleason grade heterogeneity, tumor multifocality, and biopsy undersampling. Eur Urol 66:550-560, 2014
28. Truong M, Hollenberg G, Weinberg E, et al: Impact of Gleason subtype on prostate cancer detection using multiparametric magnetic resonance imaging: Correlation with final histopathology. J Urol 198:316-321, 2017
29. Vargas H A, Akin O, Shukla-Dave A, et al: Performance characteristics of MR imaging in the evaluation of clinically low-risk prostate cancer: A prospective study. Radiology 265:478-487, 2012
30. Hurrell S L, McGarry S D, Kaczmarowski A, et al: Optimized b-value selection for the discrimination of prostate cancer grades, including the cribriform pattern, using diffusion weighted imaging. J Med Imaging (Bellingham) 5:011004, 2018
31. Le J D, Tan N, Shkolyar E, et al: Multifocality and prostate cancer detection by multiparametric magnetic resonance imaging: Correlation with whole-mount histopathology. Eur Urol 67:569-576, 2015
32. Lee D, Fontugne J, Gumpeni N, et al: Molecular alterations in prostate cancer and association with MRI features. Prostate Cancer Prostatic Dis 20:430-435, 2017

33. McCann S M, Fan X, Wang J, et al: Quantitative multiparametric MRI features and PTEN expression of peripheral zone prostate cancer: A pilot study. 206:559-565, 2016
34. Zundel W, Schindler C, Haas-Kogan D, et al: Loss of PTEN facilitates HIF-1-mediated gene expression. Genes Dev 14:391-396, 2000
35. Haffner M C, Mosbruger T, Esopi D M, et al: Tracking the clonal origin of lethal prostate cancer. J Clin Invest 123:4918-4922, 2013
36. Salmasi A, Khoshnoodi P, Felker E R, et al: A 17-gene genomic prostate score assay provides independent information on adverse pathology in the setting of combined multiparametric magnetic resonance imaging fusion targeted and systematic prostate biopsy. J Urol 200:564-572, 2018
37. Nassiri N, Natarajan S, Margolis D J, et al: Targeted prostate biopsy: Lessons learned midst the evolution of a disruptive technology. Urology 86:432-438, 2015
38. Panebianco V, Barchetti G, Simone G, et al: Negative multiparametric magnetic resonance imaging for prostate cancer: What's next? Eur Urol 74:48-54, 2018

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the medical sciences are intended to be within the scope of the following claims.

The invention claimed is:

1. A method of performing multi-parametric MRI (mpMRI) imaging on a human subject suspected of having prostate cancer, comprising:
    a) performing or having performed a nucleic acid-based detection assay to detect the level of SGK1, S100A6, DST, GSN and mRNA in a sample from a human subject;
    b) detecting a decrease in the level of SGK1, S100A6, DST, GSN and SRD5A2 mRNA in the sample from the subject as compared to that of a control sample from a subject that does not have prostate cancer, wherein the decrease in the level of the mRNAs as compared to the control sample is indicative of an increased likelihood that the subject has a mpMRI visible prostate tumor; and
    c) performing mpMRI on the subject having the decrease in the level of SGK1, S100A6, DST, GSN and SRD5A2 mRNA.

2. A method of performing a prostate cancer detection assay on a human subject suspected of having prostate cancer, comprising:
    a) performing or having performed a nucleic acid-based detection assay to detect the level of SGK1, S100A6, DST, GSN and SRD5A2 mRNA in a sample from a human subject;
    b) detecting the absence of a decrease in the level of SGK1, S100A6, DST, GSN and SRD5A2 mRNA in the sample from the human subject as compared to that of a control sample from a subject that does not have prostate cancer, wherein the absence of a decrease in the level of the mRNAs as compared to the control sample is indicative of an increased likelihood that the subject has a MRI non-visible prostate tumor; and
    c) performing a non-MRI imaging technique or a prostate biopsy on the subject having the absence of a decrease in the level of SGK1, S100A6, DST, GSN and SRD5A2 mRNA.

3. The method of claim 1, wherein said sample is tissue, urine, or blood.

4. The method of claim 3, wherein said tissue is prostate tissue.

5. The method of claim 1, wherein said prostate cancer is aggressive prostate cancer.

6. The method of claim 1, further comprising detecting altered expression of one or more of AMACR, TPM2, MYLK, or KLK2 genes in said sample.

7. The method of claim 2, further comprising detecting altered expression of one or more of AMACR, TPM2, MYLK, or KLK2 genes in said sample.

* * * * *